(12) United States Patent
Duan et al.

(10) Patent No.: US 10,093,695 B2
(45) Date of Patent: *Oct. 9, 2018

(54) STEROL DERIVATIVE, PREPARATION METHOD THEREFOR AND USE THEREOF

(71) Applicant: Beijing Peking University WBL Biotech Co., Ltd., Beijing (CN)

(72) Inventors: Zhenwen Duan, Beijing (CN); Shuren Guo, Beijing (CN); Xuemei Li, Beijing (CN)

(73) Assignee: BEIJING PEKING UNIVERSITY WBL BIOTECH CO., LTD., Beijing (CN)

(*) Notice: Subject to any disclaimer, the term of this patent is extended or adjusted under 35 U.S.C. 154(b) by 312 days.

This patent is subject to a terminal disclaimer.

(21) Appl. No.: 14/376,481

(22) PCT Filed: Feb. 4, 2013

(86) PCT No.: PCT/CN2013/071350
§ 371 (c)(1),
(2) Date: Aug. 4, 2014

(87) PCT Pub. No.: WO2013/113294
PCT Pub. Date: Aug. 8, 2013

(65) Prior Publication Data
US 2015/0025130 A1    Jan. 22, 2015

(30) Foreign Application Priority Data

Feb. 2, 2012 (CN) .......................... 2012 1 0023523
Feb. 2, 2012 (CN) .......................... 2012 1 0023584

(51) Int. Cl.
| | |
|---|---|
| *C07J 71/00* | (2006.01) |
| *A61K 31/58* | (2006.01) |
| *A61K 36/88* | (2006.01) |
| *A61K 36/064* | (2006.01) |
| *A61K 31/357* | (2006.01) |
| *A61K 36/899* | (2006.01) |

(52) U.S. Cl.
CPC .......... *C07J 71/0005* (2013.01); *A61K 31/357* (2013.01); *A61K 31/58* (2013.01); *A61K 36/064* (2013.01); *A61K 36/88* (2013.01); *A61K 36/899* (2013.01); *A61K 2236/00* (2013.01)

(58) Field of Classification Search
CPC ...... C07J 71/005; A61K 31/58; A61K 36/064; A61K 2236/00
USPC .............................................. 514/172; 540/62
See application file for complete search history.

(56) References Cited

U.S. PATENT DOCUMENTS 7,196,191 B2    3/2007    Fuchs et al.

FOREIGN PATENT DOCUMENTS

CN          101012268 A         8/2007

*Primary Examiner* — Barbara P Badio
(74) *Attorney, Agent, or Firm* — Shumaker, Loop & Kendrick, LLP; James D. Miller

(57) ABSTRACT

The present disclosure discloses a sterol derivative, a preparation method therefor and a use thereof. The sterol derivative includes a sterol compound with Structural Formula (I) or a pharmaceutically acceptable salt thereof, or an extract containing the sterol compound, or a composition containing the sterol compound, wherein Structural Formula (I) is as follows:

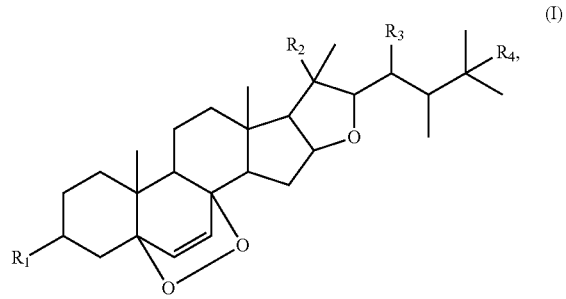

where $R_1$ is —OH, =O, H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH. The compound with Structural Formula (I) can be used for preparing a drug having inhibitory effect on 3-hydroxy-3-methylglutaryl-coenzyme A (HMG-CoA) reductase activity and the prepared drug can effectively inhibit the HMG-CoA reductase activity or be used for preparing an anti-cancer drug.

17 Claims, 9 Drawing Sheets

STEROL DERIVATIVE, PREPARATION METHOD THEREFOR AND USE THEREOF

TECHNICAL FIELD

The present disclosure relates to the field of pharmacy, and in particular to a sterol derivative with Structural Formula (I), a preparation method and a use thereof.

BACKGROUND

*Monascus*-fermented rice is a reddish purple rice starter prepared from rice fermented by *Monascus*. *Monascus*-fermented rice, which is called red yeast rice in ancient times, is prepared by fermenting rice which is inoculated with a rice raw starter or a distiller's yeast mainly containing *Monascus*. *Monascus*-fermented rice is red, thus it is also called red koji, red rice, distilled grains, and is also known as Fujian yeast and Fujian Rice etc. because it is produced in places like Fujian etc.

*Monascus*-fermented rice, which is a traditional Chinese medicine for both diet and therapy, has been widely applied in aspects of food coloring, wine making, fermentation and traditional Chinese medicines in ancient times. There are records including "red yeast rice, non-toxic with sweet taste and neutral nature" and "spleen-tonifying, vital energy-replenishing and spleen and stomach-warming" in Principles of Correct Diet; "sweet, mild and non-toxic" and "for treatment of women dysmenorrhea and postpartum lochiorrhea, and ground with wine for drinking to achieve good effect" in *Compendium of Materia Medica*, and "blood-activating, digestion-improving, spleen-tonifying and stomach-warming, for treatment of diarrhea with bloody and purulent stool and traumatic injury" etc. in *A Supplement to Augmented Materia Medica*.

Since Japanese professor Endo separated a physiological active substance monacolin K from *Monascus ruber* for the first time in the 1970s, many scholars at home or abroad have constantly found physiological active substances in *Monascus* metabolites including monacolin compounds, *Monascus* pigment, an anti-hypertension constituent γ-Aminobutyric acid (GABA) and an antioxidant constituent dimerumic acid as well as some terpenoids separated recently etc. With the development of modern biochemistry and pharmacology, effects including hypertension reduction, blood sugar reduction, obesity resistance, cancer resistance and prevention and treatment of Alzheimer's disease and osteoporosis etc. have been explored continually to add new contents to traditional *Monascus*-fermented rice. However, since there are various constituents in *Monascus*-fermented rice, people still know little about the effect of each constituent of *Monascus*-fermented rice, which limits scientific use of *Monascus*-fermented rice to a certain extent and hampers wide application of *Monascus*-fermented rice.

SUMMARY

The present disclosure separates a sterol compound with Structural Formula (I) from a *Monascus*-fermented rice preparation. The compound can be used for preparing a drug having inhibitory effect on 3-hydroxy-3-methylglutaryl-coenzyme A (HMG-CoA) reductase activity or preparing a drug having anti-cancer effect.

In an aspect of the present invention, a sterol compound with Structural Formula (I) or a pharmaceutically acceptable salt thereof is provided. Structural Formula (I) is as follows:

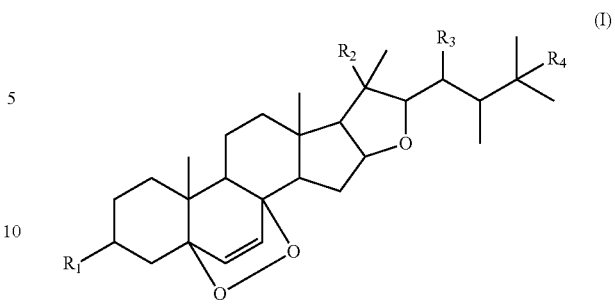

where $R_1$ is —OH, =O (carbonyl), H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH.

Further, the sterol compound or the pharmaceutically acceptable salt thereof has Structural Formula (II) which is as follows:

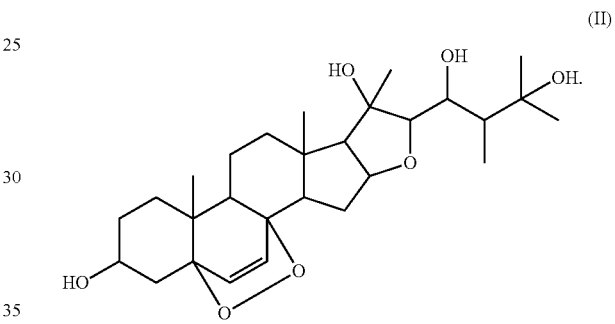

Further, in the sterol compound with Structural Formula (I) in the sterol compound or sterol compound and the pharmaceutically acceptable salt thereof, $R_1=R_2=R_3=R_4=$—OC(=O)—$CH_3$, or $R_1=R_2=R_3=R_4=$—OTs.

In another aspect of the present disclosure, a preparation method for the sterol compound with Structural Formula (I) is further provided, including the following steps: taking a *Monascus*-fermented rice preparation, performing ultrasonic extraction after adding a solvent, and concentrating an extract liquid under reduced pressure to obtain a refined extract, performing column chromatography separation for the refined extract on silica gel, performing gradient elution for the refined extract by petroleum ether and ethyl acetate during the separation process; volume ratios of petroleum ether to ethyl acetate during the gradient elution process are 75:25, 50:50 to 25:75 and 0:100 in turn; using a mixed solution of dichloromethane and methanol with a volume ratio of 1:1 as the mobile phase, performing sephadex LH-20 gel column chromatography for an eluent obtained when the volume ratio of petroleum ether to ethyl acetate is 50:50 to 25:75, combining identical parts through Thin Layer Chromatography (TLC) tracking and detection to obtain 6 parts of fractions; performing column chromatography separation for the fourth part of fractions, wherein the chromatographic column is a C18 reversed-phase silica gel column and the mobile phase is a mixed solution of methanol and water with a volume ratio of 75:25; through TLC detection, removing an impurity band and then collect the sterol compound.

Further, the preparation method further includes: performing silica gel column purification processing for the sterol compound, performing elution using a mixed solution of dichloromethane, ethyl acetate and methanol with a volume ratio of 20:20:1, and collecting the purified sterol compound after removing the impurity band.

Further, the solvent in the ultrasonic extraction process is one or more of petroleum ether, dichloromethane, ethyl acetate, ethanol, methanol or n-hexane with a volume which is 2 to 6 times as large as that of the *Monascus*-fermented rice preparation; and/or the number of extraction times during the ultrasonic extraction process is 2 to 6 times, each extraction lasts for 20 to 40 min; and/or the volume ratios of petroleum ether to ethyl acetate during the gradient elution are 75:25, 50:50, 25:75 and 0:100 in turn; sephadex LH-20 gel column chromatography is performed for an eluent obtained when the volume ratio of petroleum ether to ethyl acetate is 25:75.

In another aspect of the present disclosure, a synthesis method for a sterol compound is further provided, including: mixing and dissolving a sterol compound with Structural Formula (III) and 5,10,15,20-tetraphenylporphyrin in a solvent, introduce oxygen at −5° C. to 5° C., performing column chromatography separation after a reaction to obtain a sterol compound with Structural Formula (II),

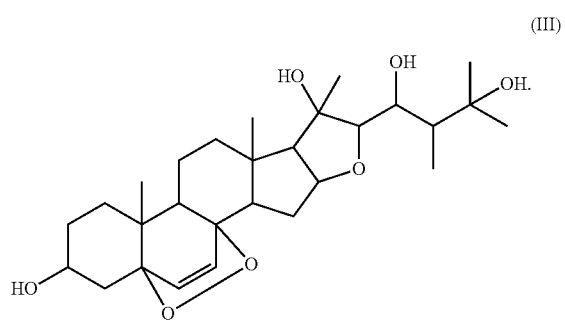 [SMILES: CC(C(O)C1OC2CC3C(C)(CCC4C35C=CC3(CC(O)CCC43C)OO5)C2C1(C)O)C(C)(C)O]

(III)

In another aspect of the present disclosure, a synthesis method for a sterol compound with Structural Formula (I) and a derivative thereof is further provided. The method includes: using a sterol compound with Structural Formula (III) as a raw material, generating ester/benzenesulfonate through derivatization and then generating the sterol compound with Structural Formula (I) through oxidation, wherein $R_1=R_2=R_3=R_4=-OC(=O)-CH_3$, or $R_1=R_2=R_3=R_4=-OTs$; or using the sterol compound with Structural Formula (III) as the raw material, generating a sterol compound with Structural Formula (II) through oxidation, and then generating the sterol compound with Structural Formula (I) through derivatization, wherein $R_1=R_2=R_3=R_4=-OC(=O)-CH_3$; or $R_1=R_2=R_3=R_4=-OTs$.

In another aspect of the present disclosure, a synthesis method for a sterol compound is further provided, when $R_1=R_2=R_3=R_4=-OC(=O)-CH_3$, the synthesis method includes: performing catalytic reaction for a sterol compound with Structural Formula (II) and acetic anhydride to obtain the $R_1=R_2=R_3=R_4=-OC(=O)-CH_3$ sterol compound; when $R_1=R_2=R_3=R_4=-OTs$, the synthesis method includes: using triethylamine as an acid removal agent, performing a reaction for the sterol compound (II) and p-toluenesulfonyl chloride with a molar ratio of 1:4 to 1:8 in dichloromethane to synthetize the $R_1=R_1=R_2=R_3=R_4=-OTs$ sterol compound; Structural Formula (II) is as follows:

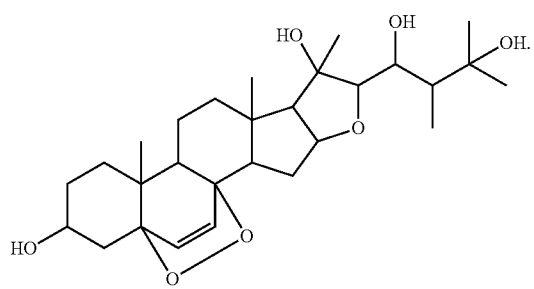

(II)

In another aspect of the present disclosure, an extract is further provided. The extract contains a sterol compound above.

Further, the extract is an extract of a *Monascus*-fermented rice preparation.

Further, the extract includes: (1) an eluent obtained when the volume ratio of petroleum ether to ethyl acetate is 50:50 to 25:75 in a gradient elution process of a preparation method for the sterol compound; (2) the fourth part of fractions obtained in a TLC tracking and detection process in the preparation method for the sterol compound; (3) a sterol compound collected after removing an impurity band through TLC detection in the preparation method for the sterol compound; or (4) a sterol compound obtained after performing purification in the preparation method for the sterol compound.

In another aspect of the present disclosure, a composition is further provided, including the sterol compounds, and/or the extract. Optionally, the composition further includes a pharmaceutically acceptable carrier or an auxiliary material.

In another aspect of the present disclosure, an application of the sterol compounds, or the extract, or the composition in preparing a drug for prevention and/or treatment/or auxiliary treatment of cancer is further provided.

Further, the anti-cancer drug in the application is an anti-hepatoma drug or an anti-lymphoma drug.

In another aspect of the present disclosure, an application of the sterol compounds, or the extract, or the composition in preparing a drug for reducing or regulating blood lipid, or preventing and/or treating dyslipidemia, hyperlipidemia, hypercholesterolemia, or atherosclerosis, or improving vascular endothelial functions, or inhibiting platelet aggregation is further provided.

In another aspect of the present disclosure, a method for inhibiting HMG-CoA reductase in vivo or in vitro is further provided, including: a step of using an effective amount of an HMG-CoA reductase inhibitor to inhibit the HMG-CoA reductase. The HMG-CoA reductase inhibitor is the sterol compounds or the extract or the composition.

In another aspect of the present disclosure, a method for inhibiting cancer cells in vivo or in vitro is further provided, including: use a cancer inhibitor to inhibit the cancer cells. The cancer cell inhibitor includes the compounds, or the extract or the composition and the cancer cells are hepatoma cells or lymphoma cells.

The present disclosure has the following beneficial effect: the present disclosure separates a compound from a *Monascus*-fermented rice preparation successfully. The compound is provided with the structure in Structural Formula (I), is able to effectively inhibit HMG-CoA reductase, and has a potential to be used as a drug for reducing or regulating blood lipid, or preventing and/or treating dyslipidemia, hyperlipidemia, hypercholesterolemia, or atherosclerosis, or improving vascular endothelial functions, or inhibiting platelet aggregation. At the same time, the compound can effectively inhibit proliferation of cancer cells (tumour cells) and the inhibitory effect is in a concentration-effect relationship so that the compound has a potential to be used as a drug for prevention and/or treatment/or auxiliary treatment of cancer.

BRIEF DESCRIPTION OF THE DRAWINGS

The accompanying drawings of the present disclosure are used for providing further understanding to the present disclosure and constitute a part of the present disclosure. The exemplary embodiments of the present disclosure and descriptions thereof are used for explaining the present disclosure and form no improper limit to the present disclosure. In the accompanying drawings.

DETAILED DESCRIPTION

Figure 1:
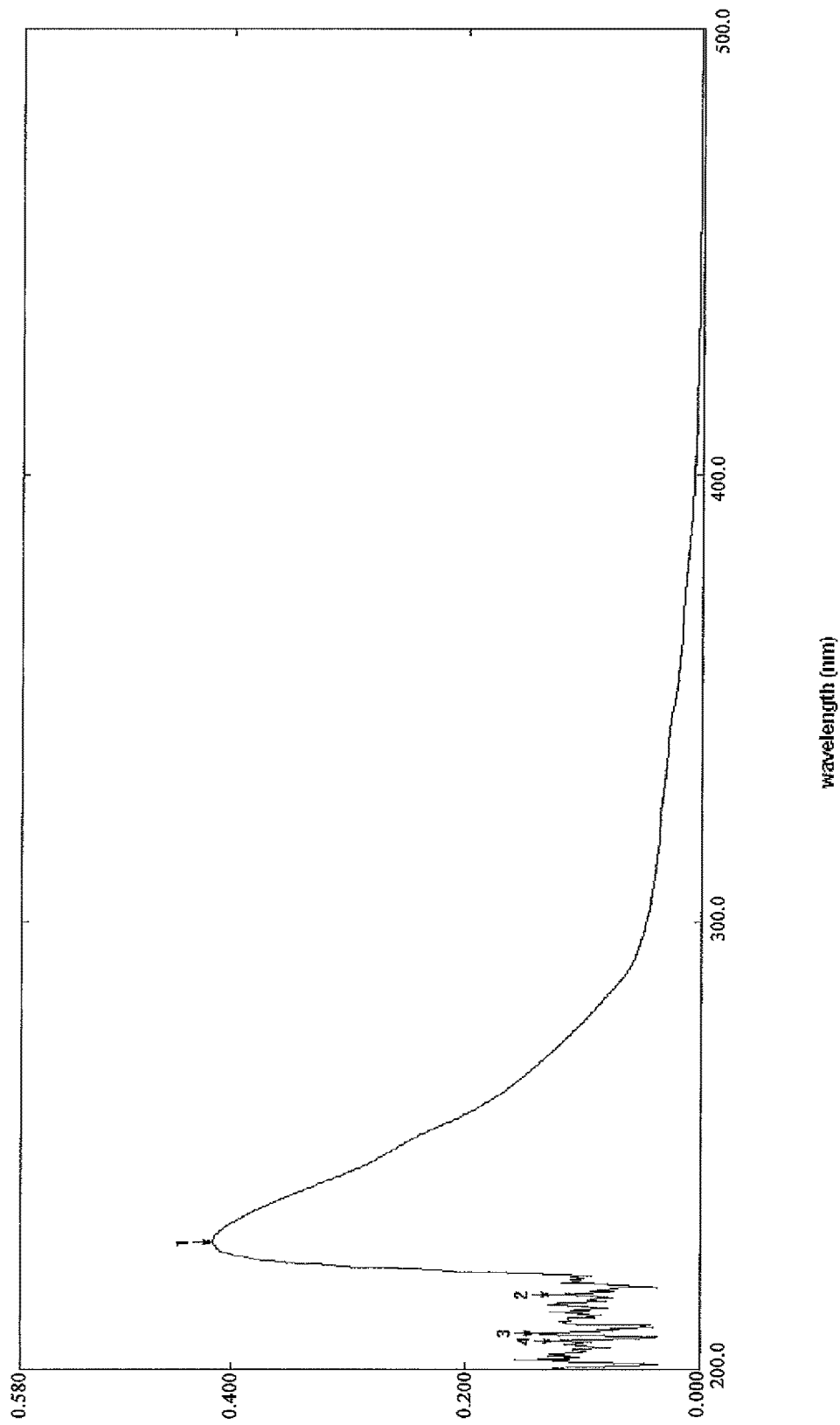
FIG. 1 shows an Ultraviolet (UV) spectrum of a compound having Structural Formula (II) and prepared in the first embodiment.

It should be noted that, if there is no conflict, the embodiments in the present application and the characteristics in the embodiments can be combined with one another. The present disclosure will be described in details below with reference to the accompanying drawings and in combination with the embodiments.

In a typical embodiment of the present disclosure, a sterol compound with Structural Formula (I) or a pharmaceutically acceptable salt thereof is provided, and Structural Formula (I) is as follows:

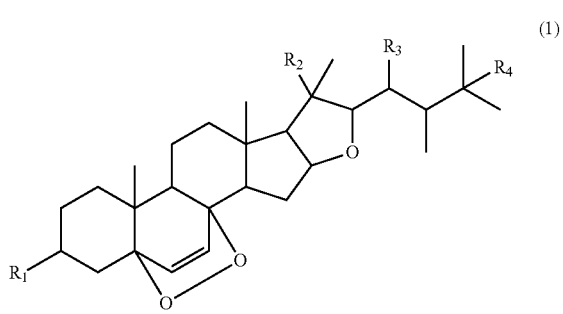

(I)

where $R_1$ is —OH, =O (carbonyl), H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH. In the present disclosure, the term "C1-C3 alkyl" includes methyl, ethyl, propyl or isopropyl.

Preferably, the sterol compound or the pharmaceutically acceptable salt thereof has Structural Formula (II) which is as follows:

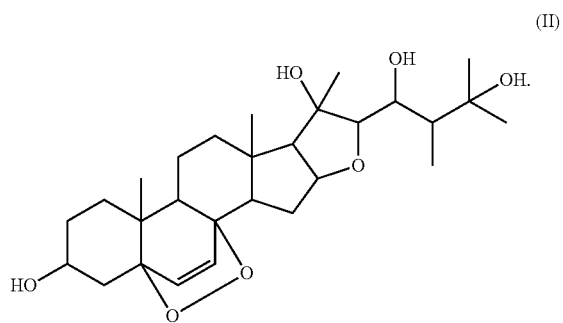 [SMILES: CC(C(O)C1OC2CC3C(C)(CCC4C35C=CC3(CC(O)CCC43C)OO5)C2C1(C)O)C(C)(C)O]

(II)

Through long-term studies, the inventor extracted a compound having the Structural Formula (I) from a *Monascus*-fermented rice preparation. The "*Monascus*-fermented rice preparation" mentioned in the present application refers to a composition or a mixture etc. containing *Monascus*-fermented rice. Those skilled in the art can rationally analyze whether a substance can be used as the *Monascus*-fermented rice preparation according to ingredients of the substance. For example, Xuezhikang Capsule prepared by Beijing Peking University WBL Biotech Co., Ltd., and *Monascus*-fermented rice powder and *Monascus*-fermented rice lyophilized powder sold on the market etc. can be used as the *Monascus*-fermented rice preparation. The compound prepared from the *Monascus*-fermented rice preparation is a brand new compound. The structural formula is provided with a sterol compound mother nucleus, an unsaturated bond and a double-oxygen bridge ring-shaped structure. There is no related report about the compound in *Monascus*-fermented rice extracts. In addition, the inventor further researched the activity of such kind of compounds, and surprisingly found that they have HMG-CoA reductase inhibitory effect and anti-cancer effect, especially on hepatoma and lymphoma.

In a typical embodiment of the present disclosure, a preparation method for the compound includes the following steps: taking a *Monascus*-fermented rice preparation, performing ultrasonic extraction after adding a solvent, and concentrating an extract liquid under reduced pressure to obtain a refined extract, performing column chromatography separation for the refined extract on silica gel, performing gradient elution for the refined extract by petroleum ether and ethyl acetate during the column chromatography separation process; volume ratios of petroleum ether to ethyl acetate during the gradient elution process are 75:25, 50:50 to 25:75 and 0:100 in turn; taking the eluted fraction of petroleum ether to ethyl acetate (50:50 to 25:75); preferably, the volume ratios of petroleum ether to ethyl acetate during the gradient elution process are 75:25, 50:50, 25:75 and 0:100 in turn and take the eluent fraction of petroleum ether to ethyl acetate (25:75); using a mixed solution of dichloromethane and methanol with a volume ratio of 1:1 as the mobile phase, performing sephadex LH-20 gel column chromatography, combining identical parts through TLC tracking and detection to obtain 6 parts of fractions; performing column chromatography separation for the fourth part of fractions, wherein the chromatographic column is a C18 reversed-phase silica gel column and the mobile phase is a mixed solution of methanol and water with a volume ratio of 75:25; through TLC detection, removing an impurity band and then collecting the sterol compound. A TLC detection condition is a normal phase silica gel plate; a developer is dichloromethane-ethyl acetate-methanol=8:8:1 and the Retardation factor (Rf) value of the sterol compound is about 0.3. The sterol compound is obtained by collecting fractions with the Rf value.

Preferably, silica gel column purification is performed for the sterol compound in the preparation method, elution is performed by a mixed solution of dichloromethane, ethyl acetate and methanol with a volume ratio of 20:20:1 and the purified sterol compound is collected after the impurity band is removed.

Preferably, the solvent in the ultrasonic extraction process in the preparation method is one or more of petroleum ether, dichloromethane, ethyl acetate, ethanol, methanol or n-hexane, preferably n-hexane. The volume of the used solvent is 2 to 6 times as large as that of the *Monascus*-fermented rice preparation. Preferably, the number of extraction times during the ultrasonic extraction process is 2 to 6 times, each extraction lasts for 20 to 40 min. Time and product content can be considered rationally in this range.

Besides the extraction method, the sterol compound with Structural Formula (I) of the present disclosure may be further prepared by an organic synthesis method. Taught by the present disclosure, those skilled in the art are able to prepare the sterol compound with Structural Formula (I) according to an existing sterol compound artificial synthesis method.

In an embodiment of the present disclosure, a preparation method for a sterol compound with Structural Formula (II) is provided. The method includes: mixing and dissolving a sterol compound with Structural Formula (III) and 5,10,15,20-tetraphenylporphyrin in a solvent, introducing oxygen at −5° C. to 5° C., performing column chromatography separation after a reaction irradiated by a projection lamp to obtain the sterol compound with Structural Formula (II),

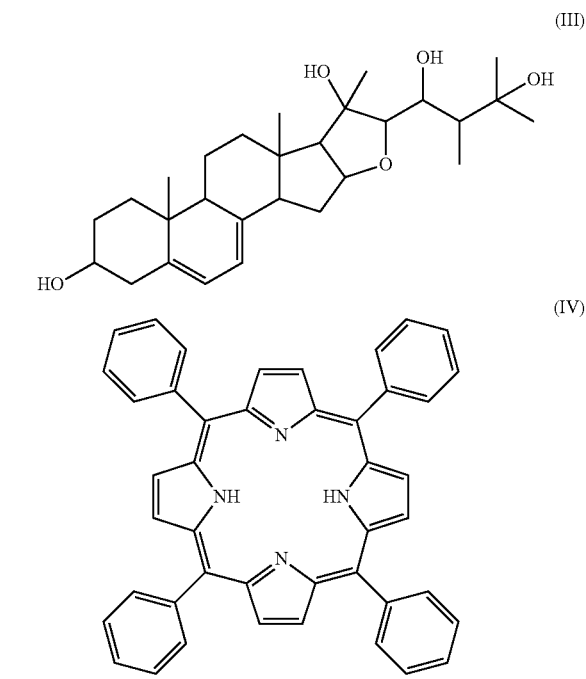

The 5,10,15,20-tetraphenylporphyrin used in the method has a structure of Structural Formula (IV) and the sterol compound with Structural Formula (III) is 16,22-epoxy-ergosta-5,7-dien-3,20,23, 25-tetraol and may be prepared by the following method:

1) performing ultrasonic extraction for about 1 kg of dry powder contained in Xuezhikang capsules (produced by Beijing Peking University WBL Biotech Co., Ltd.) for 3 times by using dichloromethane with a volume which is 2 to 6 times as large as that of the dry powder as a solvent, each ultrasonic extraction lasts for 20 to 40 minutes, combining extract liquids, concentrating under reduced pressure and recycling the solvent to obtain 91 g of a dichloromethane extract;

2) performing column chromatography separation on silica gel for 50 g of the dichloromethane extract and performing gradient elution with petroleum ether and ethyl acetate, wherein volume ratios of petroleum ether to ethyl acetate are 75:25, 50:50, 25:75 and 0:100 in turn;

3) performing separation through C18 reversed-phase column chromatography for 5.0 g of the eluted fraction of petroleum ether to ethyl acetate (25:75), and performing gradient elution with methanol-water (10:90 to 100:0) to obtain four parts (methanol-water 10:90, 50:50, 75:25, 100:0), wherein 1.3 g of a methanol-water (75:25) elution part is purified through semi-preparative high performance liquid chromatography by using acetonitrile-0.2% acetic acid aqueous solution (45:55) as the mobile phase at a flow rate of 4 mL/min and by using a C18 semi-preparative chromatographic column (10×250 mm, 5 μm) as the stationary phase; the detection wavelength of a Diode Array Detector (DAD) is 270 nm; collecting chromatographic peak with 9.2 min; performing concentration after a plurality of times of accumulation, and performing freeze-drying to obtain about 40 mg of the compound.

In an embodiment of the present disclosure, a synthesis method for a sterol compound with Structural Formula (I) and a derivative thereof is further provided, which may use a sterol compound with Structural Formula (III) as a raw material, generate ester/benzenesulfonate through derivatization, and then generate the sterol compound with Structural Formula (I) through oxidation, wherein $R_1=R_2=R_3=R_4=$—OC($=$O)—$CH_3$, or $R_1=R_2=R_3=R_4=$—OTs; or use the sterol compound with Structural Formula (III) as the raw material, generate a sterol compound with Structural Formula (II) through oxidation, and then generate the sterol compound with Structural Formula (I) through derivatization, wherein $R_1=R_2=R_3=R_4=$—OC($=$O)—$CH_3$; or $R_1=R_2=R_3=R_4=$—OTs; a method for forming an ester/benzenesulfonate bond and a double-oxygen structure may apply a conventional method in the art.

In an embodiment of the present disclosure, the synthesis method for the sterol compound with Structural Formula (I) in which $R_1=R_2=R_3=R_4=$—OC($=$O)—$CH_3$ includes: performing catalytic reaction for a sterol compound with Structural Formula (II) and acetic anhydride to obtain the $R_1=R_2=R_3=R_4=$—OC($=$O)—$CH_3$ sterol compound; preferably, the compound is prepared by a reaction for 1 to 3 hours in the presence of a catalytic amount of pyridine at 40° C. to 80° C.

In an embodiment of the present disclosure, the synthesis method for the sterol compound with Structural Formula (I) in which $R_1=R_2=R_3=R_4=$—OTs (OTs is tosyloxy) includes: using triethylamine as an acid removal agent, perform a reaction for the sterol compound (II) and p-toluenesulfonyl chloride with a molar ratio of 1:4 to 1:8 in dichloromethane to synthetize the $R_1=R_1=R_2=R_3=R_4=$—OTs sterol compound; preferably, the reaction temperature is 20° C. to 40° C.

In a typical embodiment of the present disclosure, an extract is further provided. The extract includes the sterol compound with Structural Formula (I).

Preferably, the extract is an extract of a *Monascus*-fermented rice preparation.

Preferably, the extract includes: (1) the eluted fraction of petroleum ether to ethyl acetate (50:50 to 25:75) in a gradient elution process of a preparation method for the sterol compound with Structural Formula (I) of the present disclosure; (2) the fourth part of fractions obtained in a TLC tracking and detection process in a preparation process for the sterol compound with Structural Formula (I) of the present disclosure; (3) a sterol compound collected after removing an impurity band through TLC detection in the preparation process for the sterol compound with Structural Formula (I) of the present disclosure; or (4) a sterol compound obtained after performing purification in the preparation for the sterol compound with Structural Formula (I) of the present disclosure.

In a typical embodiment of the present disclosure, a composition is further provided, including the sterol compounds, and/or the extract. Optionally, the composition further includes a pharmaceutically acceptable carrier or an auxiliary material.

Generally, the pharmaceutical composition of the present disclosure contains 0.1 to 90 wt % of a sterol compound with Structural Formula (I) or a sterol compound with Structural Formula (II) and/or a pharmaceutically acceptable salt thereof or the extract. The pharmaceutical composition may be prepared according to a method known in the art. For this purpose, the sterol compound and/or a stereoisomer with Structural Formula (I) or the sterol compound with Structural Formula (II), may be bonded with one or more solid or liquid pharmaceutical excipients and/or auxiliary agents to prepare an appropriate application form or dosage form for human if necessary.

The sterol compound with Structural Formula (I) or the sterol compound with Structural Formula (II) or a pharmaceutical composition containing the sterol compound with Structural Formula (I) or the sterol compound with Structural Formula (II) of the present disclosure may be administrated by a unit dosage form, and the administration method may be intestinal administration or non-intestinal administration, including oral administration, intramuscular administration, subcutaneous administration, nasal administration, oral mucosa administration, percutaneous administration, peritoneal administration or rectal administration etc., and the administration dosage form may be tablets, capsules, dropping pills, aerosols, pills, powder, solutions, suspensions, emulsions, granules, liposomes, transdermal agents, buccal tablets, suppositories, lyophilized powder injections etc., and may be ordinary preparations, sustained release preparations, controlled release preparations and various particle drug delivery systems. In order to prepare a unit administration dosage form into tablets, various carriers known in the art may be used broadly. Examples of the carriers include a diluent and an absorbent, such as starch, dextrin, calcium sulfate, lactose, mannitol, sucrose, sodium chloride, glucose, urea, calcium carbonate, kaolin, microcrystalline cellulose, and aluminum silicate etc.; a wetting agent and a binder, such as water, glycerol, polyethylene glycol, ethanol, propanol, starch slurry, dextrin, syrup, honey, glucose solution, gum Arabic, gelatine slurry, sodium carboxymethyl cellulose, shellac, methyl cellulose, potassium phosphate, polyvinylpyrrolidone etc.; a disintegrant, such as dry starch, alginate, agar powder, brown algae starch, sodium bicarbonate and citric acid, calcium carbonate, polyoxyethylene, sorbitan fatty acid ester, sodium lauryl sulfate, methyl cellulose, ethyl cellulose etc.; a disintegration inhibitor, such as sucrose, stearin, cacao butter, hydrogenated oil etc.; an absorption enhancer, such as quaternary ammonium salts, sodium lauryl sulfate etc.; a lubricant, such as talc, silicon dioxide, corn starch, stearates, boric acid, liquid paraffin, polyethylene glycol etc. The tablets may be further prepared into coated tablets, such as sugar-coated tablets, film-coated tablets, enteric coated tablets or double-layer tablets and multilayer tablets. In order to prepare an administration unit into a pill, various carriers known in the art may be used broadly. Examples of the carriers include, a diluent and an absorbent, such as glucose, lactose, starch, cacao butter, hydrogenated vegetable oil, polyvinylpyrrolidone, Gelucire, kaolin, talc etc.; a binder, such as gum Arabic, gum tragacanth, gelatin, ethanol, honey, liquid sugar, rice paste or batter etc.; a disintegrant, such as agar powder, dry starch, alginate, sodium dodecyl sulfate, methyl cellulose, ethyl cellulose etc.; in order to prepare the administration unit into a suppository, various carriers known in the art may be used broadly. Examples of the carriers include polyethylene glycol, lecithin, cocoa butter, higher alcohols, higher alcohol esters, gelatin, semi-synthetic glycerides etc.; In order to prepare the administration unit into a capsule, an effective ingredient the sterol compound with Structural Formula (I) or the stereoisomer thereof is mixed with various carriers above, and a mixture obtained therefrom is put in a hard gelatine capsule or a soft capsule. Or the effective ingredient the sterol compound with Structural Formula (I) or the stereoisomer thereof may be prepared into a microcapsule, or suspended in an aqueous medium to form a suspension, or may be also packaged into a hard capsule or prepared into an injection to be applied. In order to prepare the administration unit into an injection, such as a solution, an emulsion, a lyophilized powder injection, and a suspension, all diluents commonly used in the art may be used, such as water, ethanol, polyethylene glycol, 1,3-propylene glycol, ethoxylated isostearyl alcohol, polyoxidized isostearyl alcohol, polyoxyethylene sorbitol fatty acid esters etc. In addition, in order to prepare an isotonic injection, a proper amount of sodium chloride, glucose or glycerol may be added in the injection. In addition, a regular cosolvent, buffer or pH regulator etc. may be further added.

In addition, a colorant, a preservative, a spice, a flavoring agent, a sweetener or other materials may be added in to a pharmaceutical preparation if necessary.

The administration dosage of the sterol compound with Structural Formula (I) or the sterol compound with Structural Formula (II) or the pharmaceutically acceptable salt thereof of the present disclosure depends on many factors. For example, the nature or severity of a disease to be prevented or treated, the gender, age, bodyweight, and individual reactions of a patient or an animal, a specific used compound, an administration method, and the number of administration times etc. The dosage may be a single dosage form or administrated by two, three or four dosage forms.

For the composition, the actual dosage levels of active ingredients in the pharmaceutical composition of the present disclosure may be changed so that the obtained amount of an active compound can effectively achieve a required therapeutic response for a specific patient, composition or administration method. The dosage levels should be selected according to the activity and administration method of a specific compound, the severity of a disease condition to be treated, and the disease conditions and medical history of a patient to be treated. However, a method in the prior art is to increase the dosage of the compound gradually from a level lower than that required to achieve a required therapeutic effect until the required effect is achieved.

When applied to the treatment and/or prevention or auxiliary treatment, a compound with an effective amount for treatment and/or prevention of the present disclosure may be applied in a pure form, or applied in a form of a pharmaceutically acceptable ester or a prodrug (if any). Or the compound may be administered as a pharmaceutical composition containing the target compound and one or more pharmaceutically acceptable excipients. The term "effective amount" refers to a dosage which is able to treat, prevent, alleviate and/or relieve the diseases or symptoms of the present disclosure in a subject. However, it should be realized that the total daily dosage of the compounds and composition of the present disclosure should be decided by an attending doctor in a reliable medical judgment scope. For any specific patient, a specific therapeutic effective dosage level is determined according to many factors. The factors include a treated disorder, and the severity of the disorder; the activity of a specific used compound; the specific used composition, the age, bodyweight, general health conditions, gender and diet of a patient; the administration time, administration method and excretion rate of the specific used compound; the duration of treatment; medicines used in combination with or used simultaneously with the specific used compound; and similar known factors in the medical field. For example, a method of the art is to increase the dosage of the compound gradually from a level lower than that required to achieve a required therapeutic effect until the required effect is achieved. Generally, the dosage of the sterol compound with Structural Formula (I) of the present disclosure for mammals, especially human may be 0.001 to 1000 mg/kg bodyweight/day, e.g. 0.01 to 100 mg/kg bodyweight/day or 0.01 to 10 mg/kg bodyweight/day.

In a typical embodiment of the present disclosure, an application of the sterol compounds, or the extract, or the composition in preparing a drug for prevention and/or treatment/or auxiliary treatment of cancer is further provided. Specifically, the cancer is hepatoma or lymphoma.

In a typical embodiment of the present disclosure, an application of the sterol compounds, or the extract, or the composition in preparing a drug for reducing or regulating blood lipid, or preventing and/or treating dyslipidemia, hyperlipidemia, hypercholesterolemia, or atherosclerosis, or improving vascular endothelial functions, or inhibiting platelet aggregation is provided.

In a typical embodiment of the present disclosure, a method for inhibiting HMG-CoA reductase in vivo or in vitro is further provided, including: use an effective amount of an HMG-CoA reductase inhibitor to inhibit the HMG-CoA reductase. The HMG-CoA reductase inhibitor is the sterol compounds or the extract or the composition.

In a typical embodiment of the present disclosure, a method for inhibiting cancer cells in vivo or in vitro is further provided, including: use a cancer inhibitor to inhibit the cancer cells. The cancer cell inhibitor includes a sterol derivative. The sterol derivative includes a sterol compound with Structural Formula (I), a pharmaceutically acceptable salt thereof, an extract containing the sterol compound, or a composition containing the sterol compound. The cancer cells are preferably hepatoma cells or lymphoma cells.

The inhibitory effect of a sterol compound with Structural Formula (I) of the present disclosure on HMG-CoA reductase activity and the anti-cancer effect of the compound will be described in details below in combination with the first embodiment to the third embodiment.

Methods for Preparing a Sterol Compound with Structural Formula (II)

Embodiment 1

Raw material: 2 kg of contents of Xuezhikang capsules prepared by Beijing Peking University WBL Biotech Co., Ltd.

Embodiment 2

Raw material: 3 kg of *Monascus*-fermented rice powder sold on the market.

A Method for Preparing the Sterol Compound with Structural Formula (II) by Using the Raw Materials in the First Embodiment and the Second Embodiment Respectively:

1) perform ultrasonic extraction for 2 kg of the contents of the Xuezhikang capsules or about 3 kg of the *Monascus*-fermented rice powder for 3 times with n-hexane with a volume which is 2 to 6 times as large as that of the contents of the Xuezhikang capsules or the *Monascus*-fermented rice powder as a solvent, each ultrasonic extraction lasts for 20 to 40 minutes, combine extract liquids, and concentrate under reduced pressure to obtain 84 g of an n-hexane refined extract;

2) perform column chromatography separation for 50 g of the n-hexane refined extract on silica gel, perform gradient elution by petroleum ether and ethyl acetate; volume ratios of petroleum ether to ethyl acetate are 75:25, 50:50, 25:75 and 0:100 in turn;

3) concentrate the eluted fraction of petroleum ether-ethyl acetate (75:25) under reduced pressure to obtain 3 g of an oily substance; dissolve the oily substance with a trace amount of dichloromethane-methanol (1:1) and perform sephadex LH-20 silica gel column chromatography on a column by using dichloromethane and methanol (1:1) as the mobile phase; 120 fractions are received in total and each fraction is 5 mL; combine identical parts through TLC tracking and detection to obtain 6 parts, namely fractions 1 to 50; 51 to 75; 76 to 80; 81 to 93; 94 to 110, and 111 to 120 respectively; concentrate the fourth part (fractions 81 to 93) under reduced pressure to obtain 1.55 g of an oily substance; dissolve the oily substance with a trace amount of 100% methanol and perform elution with methanol and water (75:25) on a C18 reversed-phase silica gel column; according to TLC detection results, collect fractions of the compound, and dry and concentrate the fractions to obtain the crude sterol compound; wherein TLC detection condition is a normal phase silica gel plate, a developer is dichloromethane-ethyl acetate-methanol=8:8:1 and the Rf value of the sterol compound is about 0.3. The crude sterol compound is obtained by collecting fractions with the Rf value. In order to further purify the crude compound, perform silica gel column chromatography by using dichloromethane:ethyl acetate:methanol (20:20:1) elution system and finally obtain 5 mg of the purified compound.

Embodiment 3

A Chemical Synthesis Method for a Sterol Compound with Structural Formula (II):
a sterol compound with Structural Formula (III) is used as a raw material:
An extraction method of the sterol compound with Structural Formula (III) is described as follows:
1) perform ultrasonic extraction for about 1 kg of dry powder contained in Xuezhikang capsules (produced by Beijing Peking University WBL Biotech Co., Ltd.) for 3 times by using dichloromethane with a volume which is 2 to 6 times as large as that of the dry powder as a solvent, each ultrasonic extraction lasts for 20 to 40 minutes, combine extract liquids, concentrate under reduced pressure and recycle the solvent to obtain 91 g of a dichloromethane refined extract;
2) perform column chromatography separation on silica gel for 50 g of the dichloromethane refined extract and perform gradient elution with petroleum ether and ethyl acetate, wherein volume ratios of petroleum ether to ethyl acetate are 75:25, 50:50, 25:75 and 0:100 in turn;
3) perform separation through C18 reversed-phase column chromatography for 5.0 g of the eluted fraction of petroleum ether-ethyl acetate (25:75), and perform gradient elution with methanol-water (10:90 to 100:0) to obtain four parts (methanol-water 10:90, 50:50, 75:25, 100:0), wherein 1.3 g of a methanol-water (75:25) elution part is purified through semi-preparative high performance liquid chromatography by using acetonitrile-0.2% acetic acid aqueous solution (45:55) as the mobile phase at a flow rate of 4 mL/min and by using a C18 semi-preparative chromatographic column (10×250 mm, 5 μm) as the stationary phase; the detection wavelength of a DAD is 270 nm; collect chromatographic peak with 9.2 min; concentrate, and freeze-dry after a plurality of times of accumulation, and finally obtain about 40 mg of the compound.
A Synthesis Method for the Sterol Compound with Structural Formula (II):

dissolve the sterol compound with Structural Formula (III) (23.49 g, 50.97 mmol) and 5,10,15,20-tetraphenylporphyrin (31.33 mg, 50.97 μmol) in 200 ml of carbon tetrachloride, introduce oxygen at 00° C.; 5 minutes later, perform a reaction for 7 hours, irradiated by a 450 W projection lamp and perform column chromatography separation to obtain the product compound (II).

Structure Identification Methods for the Compound Prepared by the First Embodiment, the Second Embodiment and the Third Embodiment are as Follows:

1. Physical and Chemical Data of the Compound

Figure 2:
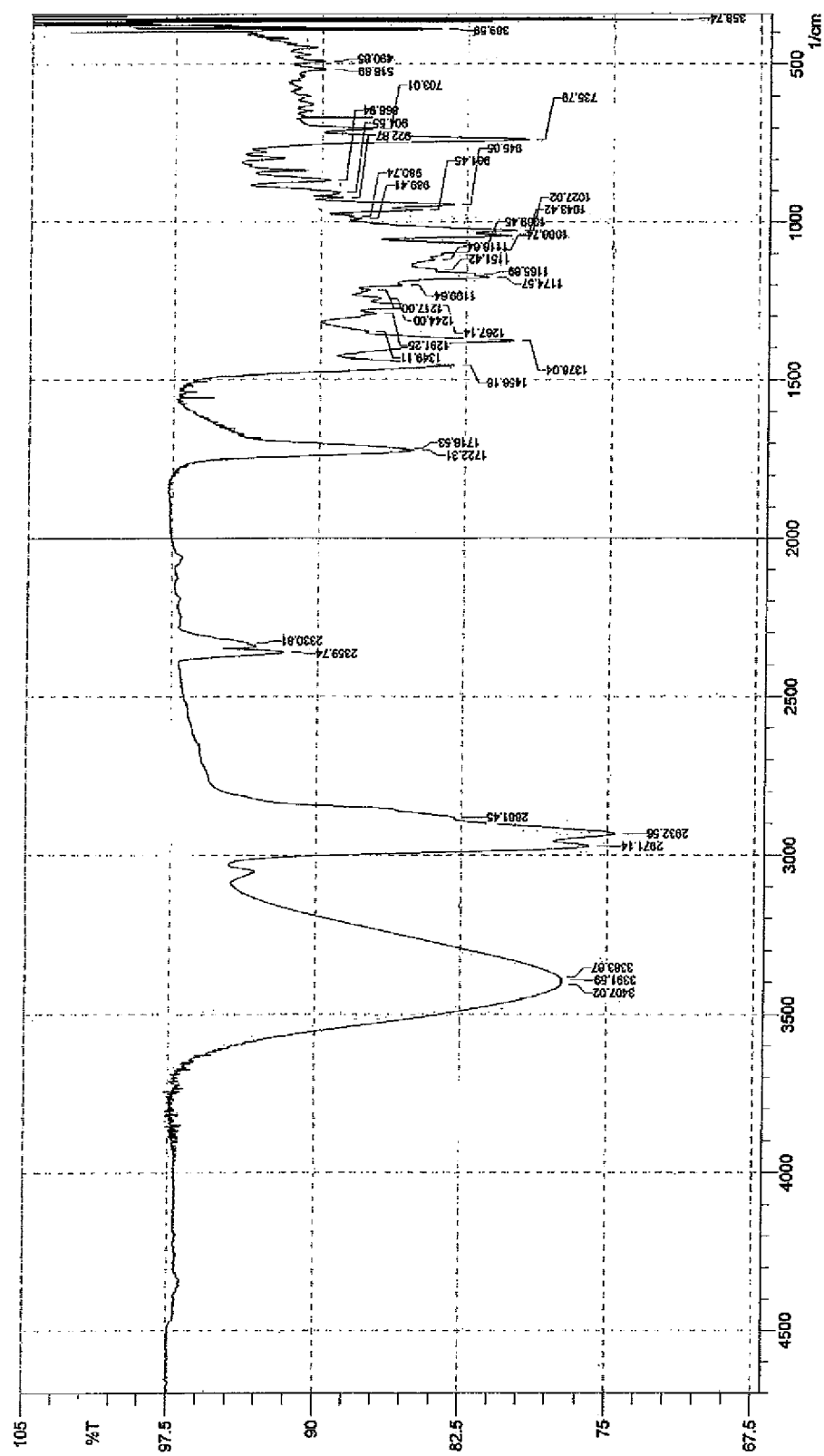
FIG. 2 shows an infrared (IR) spectrum of a compound having Structural Formula (II) and prepared in the first embodiment.

The compound prepared by the first embodiment to the third embodiment is a colorless oily substance with a specific rotation of $[\alpha]^{25}_D$ −21.59 (c 0.082, $CH_2Cl_2$:MeOH=1:1). As shown in FIG. 1, the compound prepared by the first embodiment to the third embodiment has a maximum absorption peak $\lambda_{max}$ ($CH_2Cl_2$:MeOH) of 228.40 nm in a UV spectrum. As shown in FIG. 2, the FT-IR (KBr, cm$^{-1}$) spectrum of the compound prepared by the first embodiment to the third embodiment: 3391 (—OH), 2971, 2932 (saturated hydrocarbon), 1722 (C=C), 1456, 1378 (gem-dimethyl), 1043, 945 (—O—O—).

Figure 3:
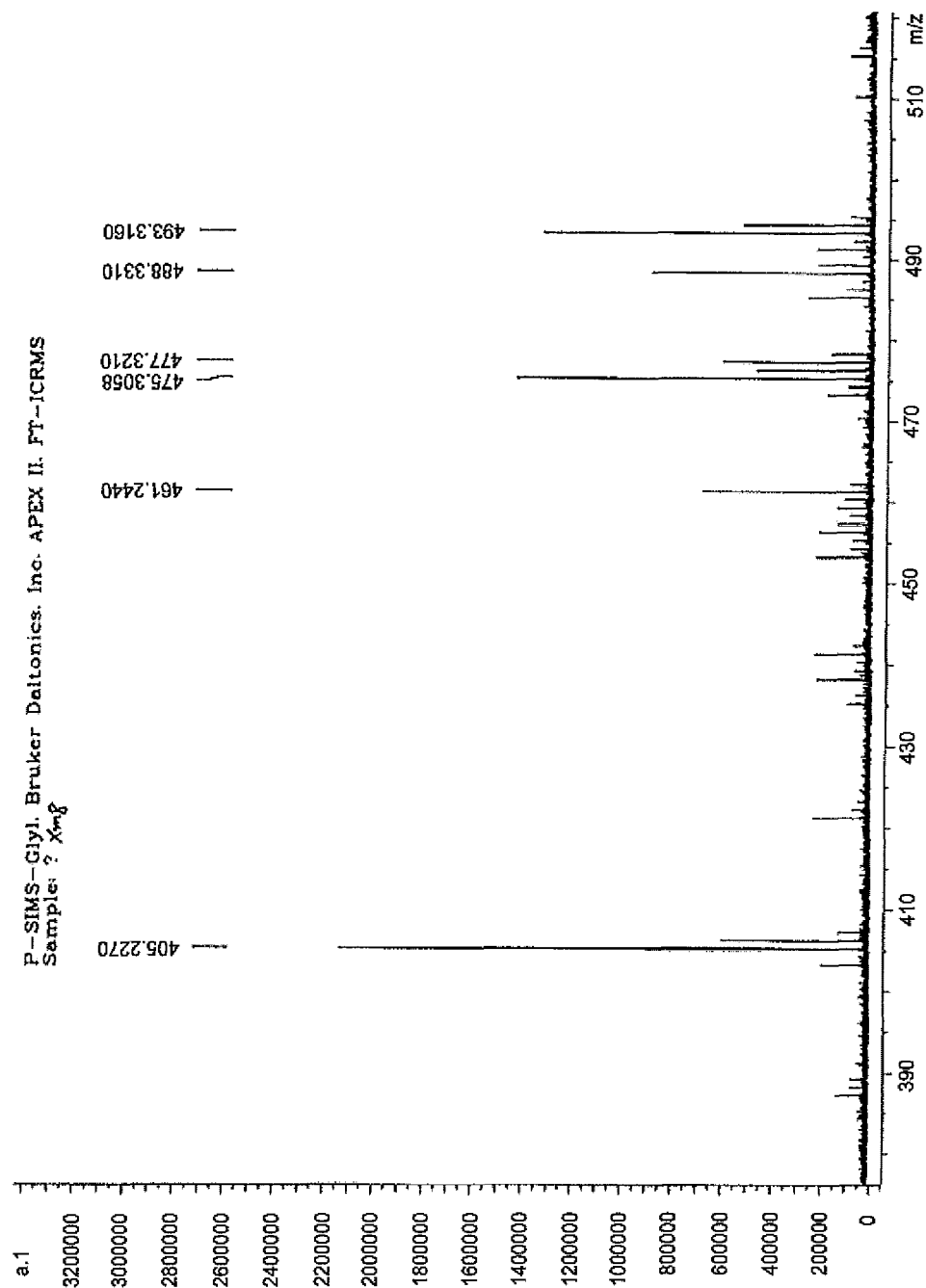
FIG. 3 shows a high resolution mass spectrum of a compound having Structural Formula (II) and prepared in the first embodiment.
Figure 4:
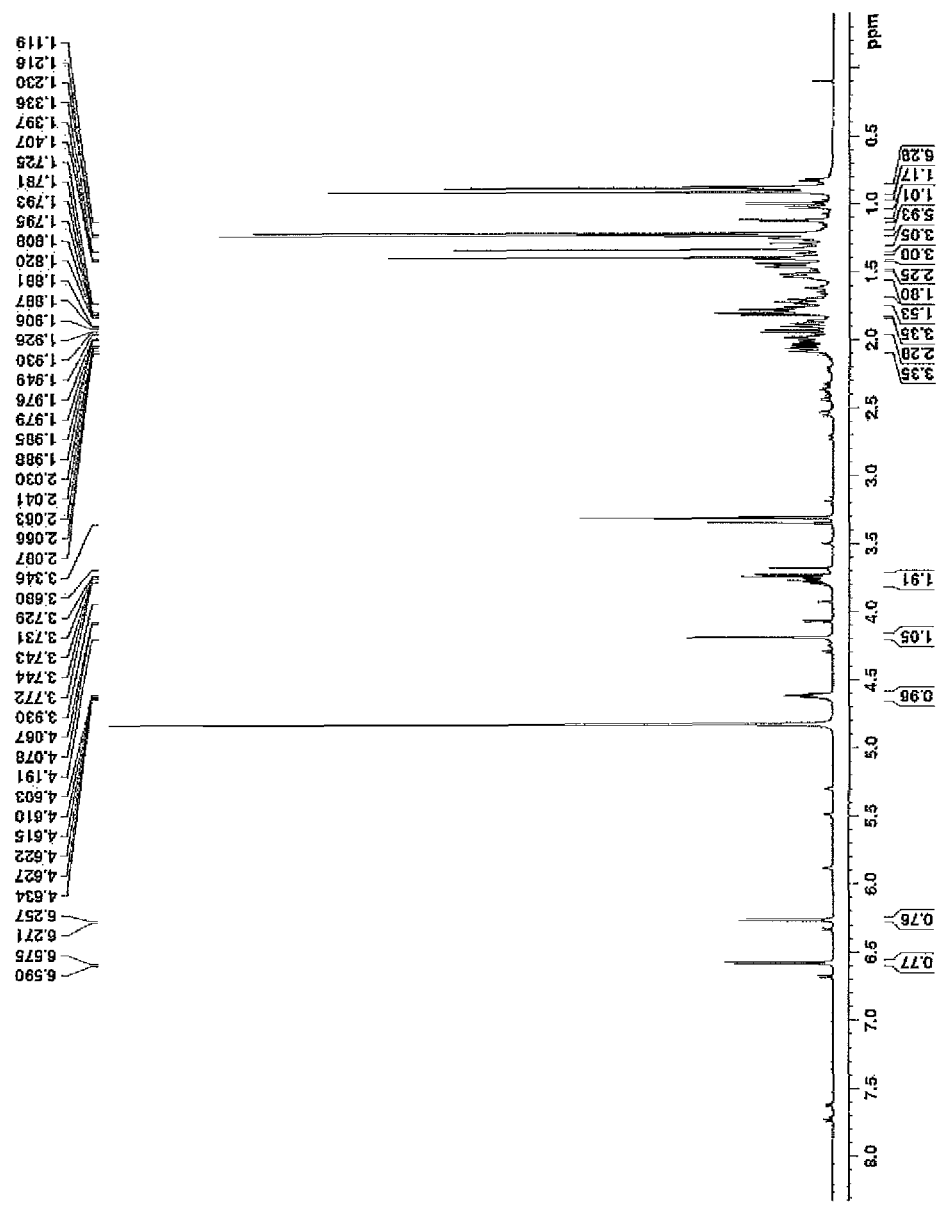
FIG. 4 shows a $^1$H-NMR (hydrogen-1 nuclear magnetic resonance) spectrum of a compound having Structural Formula (II) and prepared in the first embodiment.
Figure 5:
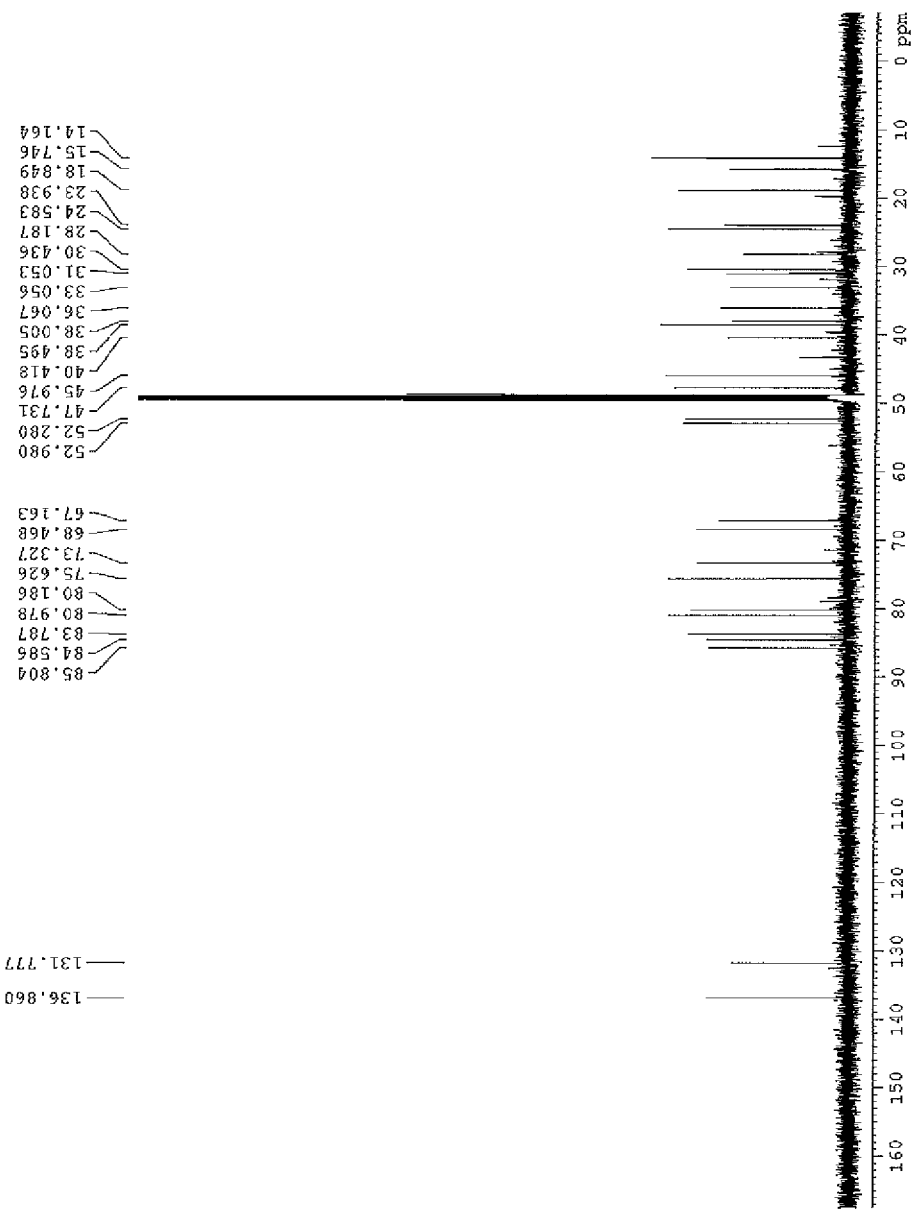
FIG. 5 shows a $^{13}$C-NMR (carbon-13 nuclear magnetic resonance) spectrum of a compound having Structural Formula (II) and prepared in the first embodiment.
Figure 6:
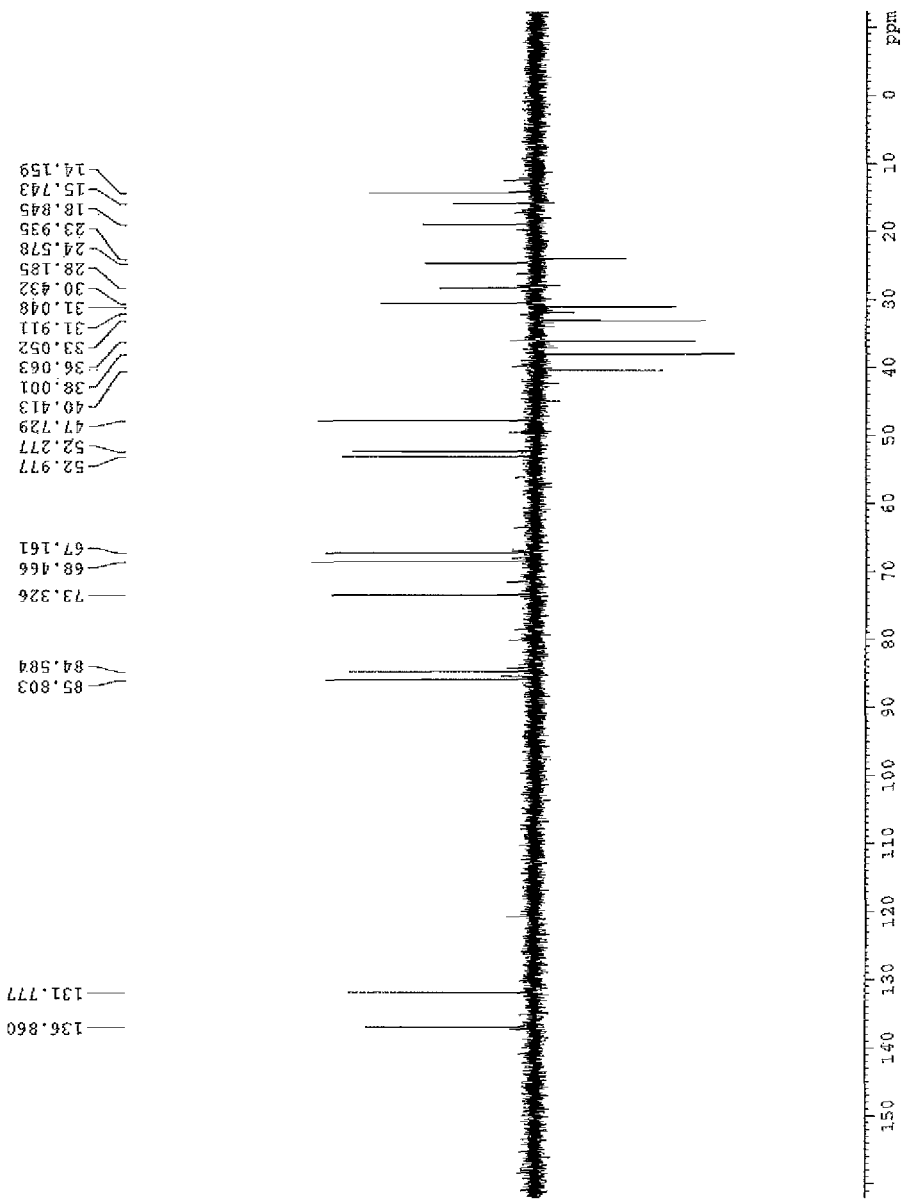
FIG. 6 shows a DEPT (Distortionless Enhancement by Polarization Transfer) spectrum of a compound having Structural Formula (II) and prepared in the first embodiment.
Figure 7:
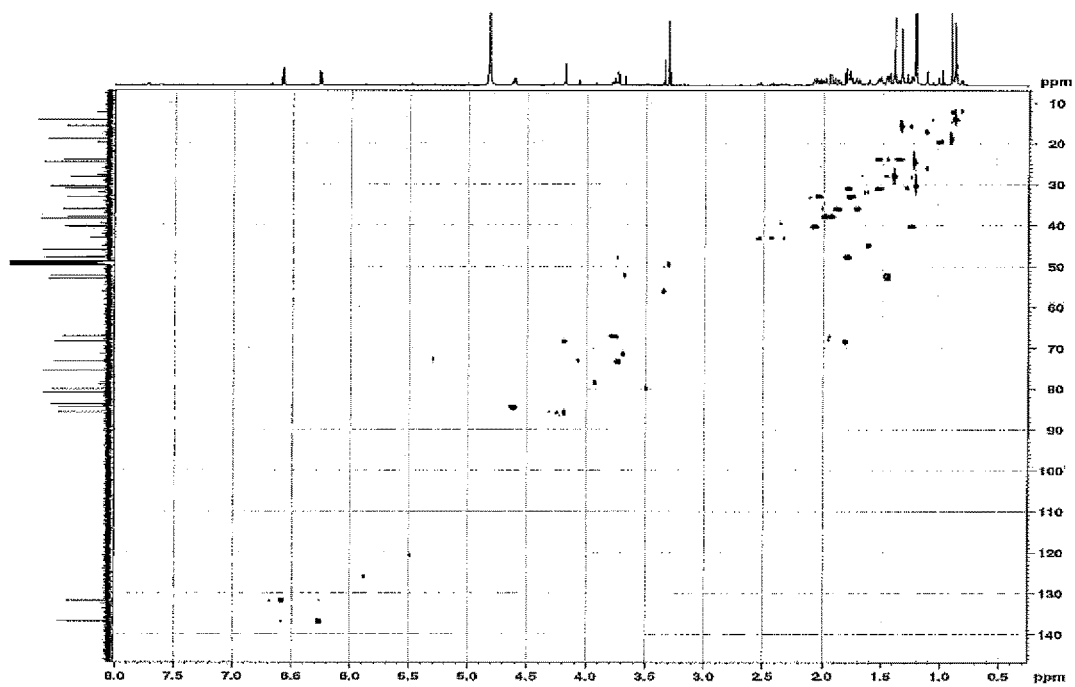
FIG. 7 shows a HSQC (Heteronuclear Singular Quantum Correlation) spectrum of a compound having Structural Formula (II) and prepared in the first embodiment.

2. Determination of the Molecular Formula of the Compound Prepared by the First Embodiment, the Second Embodiment and the Third Embodiment As shown in FIG. 3, it can be inferred from m/z 493.31596 [M+H]+(calcd. 493.31665, err 0.69) provided by Fourier Transform Ion Cyclotron Resonance Mass Spectrometry (FT-ICR-MS) that the molecular weight of the compound is 492.31. As shown in $^1$H-NMR spectrum of FIG. 4 and $^{13}$C-NMR spectrum of FIG. 5, there are 40 hydrogen signals and 28 carbon signals in total. DEPT spectrum of FIG. 6 shows that there are 6 quaternary carbons, 10 CHs, 6 $CH_2$s and 6 $CH_3$s. In the $^{13}$C-NMR spectrum of FIG. 5, two olefinic carbon signals at 136.9 ppm (C-6) and 131.8 ppm (C-7) show that the compound has a double-bond. It can be analyzed by combining HSQC spectrum of FIG. 7 and $^{13}$C-NMR spectrum of FIG. 5 that there are 8 carbons connected with oxygen atoms at 67.2 ppm, 83.8 ppm, 80.2 ppm, 84.6 ppm, 81.0 ppm, 85.8 ppm, 73.3 ppm, and 75.6 ppm. Combining the molecular weight with $^1$H-NMR spectrum of FIG. 4, $^{13}$C-NMR spectrum of FIG. 5 and DEPT spectrum of FIG. 6, the molecular weight is more than 492.31 if the compound has 8 oxygen atoms, thus it can be deduced that the compound has 7 oxygen atoms and 4 hydrogen atoms which have not exhibit hydrogen signals. Thus it can be determined that 4 oxygen atoms among the 7 oxygen atoms belong to 4 hydroxyls and the remaining 3 oxygen atoms exist in non-hydroxyl forms. According to the analysis it can be determined that there are 28 carbon atoms, 44 hydrogen atoms and 7 oxygen atoms in the molecule and the molecular formula is $C_{28}H_{44}O_7$.

Figure 8:
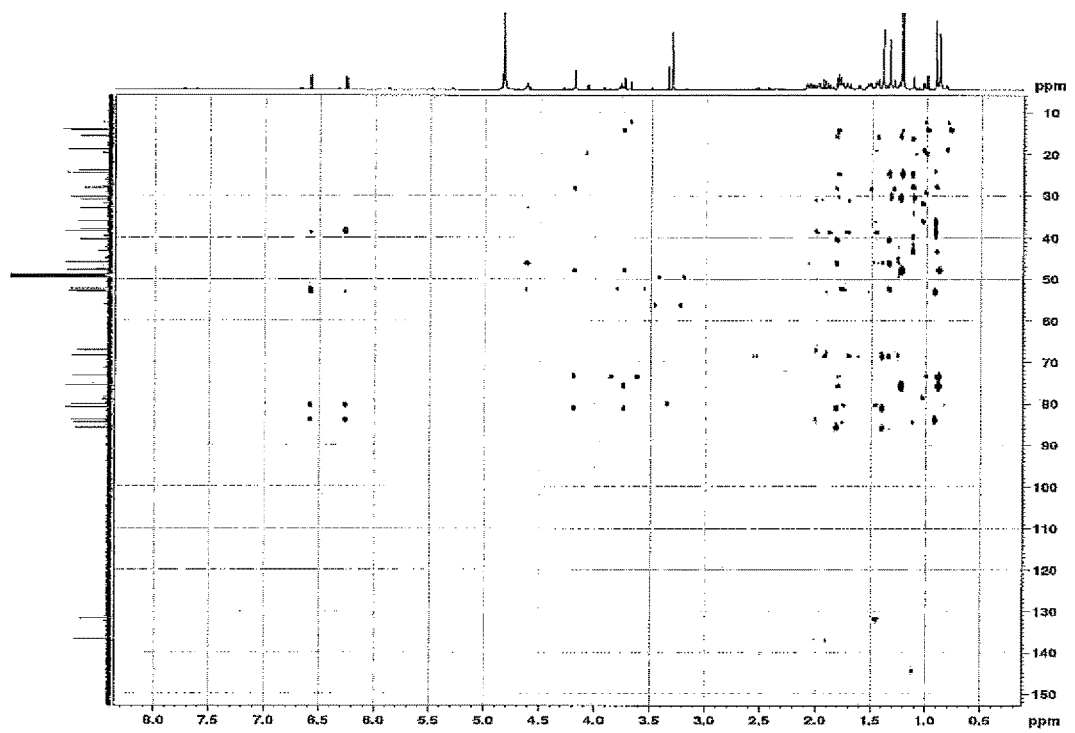
FIG. 8 shows a HMBC (Heteronuclear Multiple-Bond Correlation) spectrum of a compound having Structural Formula (II) and prepared in the first embodiment.

3. Determination of the Structural Formula of the Compound Prepared by the First Embodiment, the Second Embodiment and the Third Embodiment It is analyzed through carbon spectroscopy ($^{13}$C-NMR and DEPT) of the compound that there are 28 carbon atoms, and 6 of them are methyls and 2 of them are olefinic carbons. In addition, as shown by a UV spectrum of the compound in FIG. 1, the UV spectrum is very similar to a UV spectrum of ergosterol peroxide. It is preliminarily inferred that the compound is provided with an ergosterol peroxide framework and a —O—O— peroxide part. Thus it can be concluded that 2 oxygen atoms of 3 non-hydroxyl oxygen atoms belong to —O—O—. It can be analyzed by combining HSQC spectrum of FIG. 7 and HMBC spectrum of FIG. 8 that 8 carbons connected with the oxygen atoms belong to 4 carbons (67.2, 73.3, 75.6 and 81.0 ppm) connected with 4 hydroxyls, 2 carbons (80.2 and 83.8 ppm) connected with —O—O— and 2 carbons (84.6 and 85.8 pp) connected with the seventh oxygen atoms. It can be calculated through the molecular formula that the degree of unsaturation is 7. Thus it can be inferred that, besides 6 unsaturated sites at 1 double-bond and 5 rings of the sterol peroxide framework, the compound further has an unsaturated site which can be only a ring. Thus, it can be determined that the ring is a 5-membered ring which takes the seventh oxygen atom as the center and comprises 4 carbon atoms, C-16 (84.6 ppm), C-17 (68.5 ppm), C-20 (81.0 ppm) and C-22 (85.8 ppm). This not only satisfies the degree of unsaturation, but also satisfies the number of carbon atoms connected with the oxygen atoms. The molecular weight and the molecular formula provided with a mass spectrometry analysis system are further analyzed to verify the analysis above. It can be concluded based on the analysis above that the compound is: 5,8-epidioxy-16,22-epoxy-ergosta-6-en-3,20,23,25-tetrol 4. The Structural Formula of the Compound Prepared by the First Embodiment and the Second Embodiment is as Follows:

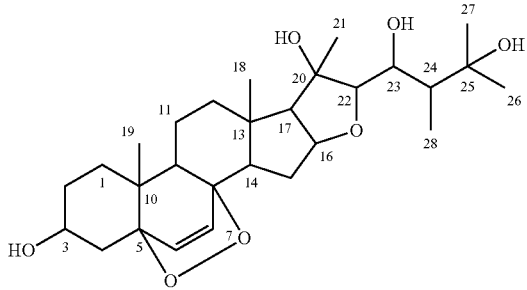 [SMILES: CC(C(O)C1OC2CC3C(C)(CCC4C35C=CC3(CC(O)CCC43C)OO5)C2C1(C)O)C(C)(C)O]

II Preparation of a Derivative of the Sterol Compound with Structural Formula (II):

The following fourth embodiment to the seventh embodiment describe a sterol compound further synthetized by using the sterol compound with Structural Formula (II) prepared by the first embodiment to the third embodiment as a raw material.

Embodiment 4

A Method for Synthetizing a Sterol Compound (Compound 4) with Structural Formula (I) in which $R_1=R_2=R_3=R_4=$—OC(=O)—CH$_3$:

heat a mixed liquid of 20 mL of acetic anhydride, the sterol compound (4.24 g, 9.2 mmol) with Structural Formula (II) prepared in the first embodiment and 3 drops of pyridine (each drop is about 40 to 50 μL) in a water bath to 50° C. and react for 2 hours, cool the mixed liquid and add a saturated NaHCO$_3$ aqueous solution, extract for 3 times with toluene, perform rotary evaporation for an organic layer to obtain a finished product, and perform column chromatography to obtain a tetraacetate of a compound (II), i.e. the sterol compound with Structural Formula (I) in which $R_1=R_2=R_3=R_4=$—OC(=O)—CH$_3$.

A structure identification method for the compound synthetized by the fourth embodiment is:

analyze $^1$H-NMR spectrum of the compound to find based on the structure of the sterol compound with Structural Formula (II) that there are 4 methyl signals at 2.06 ppm (each, 3H, S, OAc) and that other signals are substantially consistent with the hydrogen signals in Structural Formula (II). It means that there are 4 acetoxyls in the compound, i.e. the tetraacetate of Structural Formula (II) is synthetized successfully. It is further verified through Electrospray Ionization Mass Spectrometry (ESI-MS): m/z 683.36 [M+Na]$^+$ that the compound has the structure above.

Embodiment 5

A Method for Synthetizing a Sterol Compound (Compound 5) with Structural Formula (I) in which $R_1=R_2=R_3=R_4=$—OTs:

add the sterol compound (4.24 g, 9.2 mmol) with Structural Formula (II) prepared in the second embodiment and 50 mL of dry dichloromethane to a 250 mL flask, cool to 0° C., add p-toluenesulfonyl chloride (10.56 g, 55.3 mmol), add triethylamine (7.46 g, 73.6 mmol) dropwise while stirring, after the dropwise addition, stir for 1 hours at 20° C., wash the reaction mixed liquid with water (50 mL×3), dry with anhydrous sodium sulfate, filter, evaporate a solvent to dryness to obtain a crude product, and perform rapid column chromatography to obtain tetra (p-toluenesulfonyl ester) of the compound (II), i.e. the sterol compound sterol compound with Structural Formula (I) in which $R_1=R_2=R_3=R_4=$—OTs.

A structure identification method for the compound synthetized by the fifth embodiment is:

based on the structure of the sterol compound with Structural Formula (II), analyze $^1$H-NMR spectrum of the compound to find that there are 16 aromatic hydrogen signals at 7.20-7.90 ppm (16H, m, Ar) and 4 methyl signals at 2.45 ppm (each, 3H, S, Ar—CH$_3$, and other signals are substantially consistent with hydrogen signals in Structural Formula (II). It means that there are 4-OTs in the compound and tetra (p-toluenesulfonyl ester) of Structural Formula (II) is synthetized successfully. It is further verified through ESI-MS: m/z 1109.32 [M+H]$^+$ that the compound has the structure above.

III HMG-CoA Reductase Inhibitory Activity Experiment of the Compounds Prepared by the First Embodiment, the Fourth Embodiment and the Fifth Embodiment 1. Experiment Materials 1.1. Test Samples The compounds prepared by the first embodiment, the fourth embodiment and the fifth embodiment (hereinafter referred to as compound with Structural Formula (II), Compound 4 and Compound 5); a lovastatin reference substance (purchased from Sigma)

1.2 Enzyme

Rat liver microsomes (HMG-CoA reductase) that may be commercially available or prepared with reference to the following method: take out a male rat liver, after washing the male rat liver with a KESD buffer solution, perform 1200 g centrifugation for 15 minutes, take the supernatant, after performing 105000 g centrifugation again for 90 minutes twice, collect centrifugation sediments, add 8.3% glycerol to the centrifugation sediments, heating for 1 hour with a 37° C. warm bath, purify coarse rat liver microsomes with saturated ammonium sulfate, and collect 35-50% of the purified part. The obtained purified part may be stored in a refrigerator at −80° C.

1.3 Reagents

Potassium chloride, potassium dihydrogen phosphate, ethylenediaminetetraacetic acid and dithiothreitol purchased from Beijing Chemical Reagents Co., Ltd.;

Nicotinamide Adenine Dinucleotide (NADPH) purchased from Merck;

3-hydroxy-3-methylglutaryl-coenzyme A (HMG-CoA), purchased from Sigma.

2. Experiment Method

Dissolve 5.0 mg of the compound with Structural Formula (II) prepared in the first embodiment, Compound 4 or Compound 5, and 2.0 mg of lovastatin with 1 mL of a 75% ethanol solution, respectively;

the total volume of measurement system is 250 μL and the concentrations of the constituents are: potassium chloride 200 mM, potassium dihydrogen phosphate 160 mM, ethylenediaminetetraacetic acid 4 mM and dithiothreitol 10 mM; the concentrations of two substrates NADPH and HMG-CoA are respectively 200 μM and 50 μM, pH6.8, enzyme 30 μL.

Add an ethanol solution with 5 μL of the compound prepared by the first embodiment or an ethanol solution of Compound 4 or an ethanol solution of Compound 5 to a test group, add 5 μL of a lovastatin ethanol solution to a positive control group; add 5 μL of 75% ethanol to a blank control group; detect dynamic change of $OD_{340}$ on a Versamax microplate reader at 37° C., and evaluate the HMG-CoA reductase activity level by detecting the decreasing speed (represented by a slope value) of $OD_{340}$ within 5 minutes to further evaluate the enzyme inhibitory activity level, the result is as shown in Table 1.

3. Experiment Result

TABLE 1

| Sample name | Inhibitor concentration (mg/mL) | Inhibitor volume(μL) | Final concentration in the system (μg/mL) | Slope | Inhibitory rate (%) |
|---|---|---|---|---|---|
| Blank control | — | — | — | 15.6 | — |
| Lovastatin | 2.0 | 5 | 40 | 9.0 | 42.3 |
| Compound with Structural Formula (II) | 5.0 | 5 | 100 | 10.7 | 31.4 |
| Compound 4 | 5.0 | 5 | 100 | 9.7 | 37.8 |
| Compound 5 | 5.0 | 5 | 100 | 10.3 | 34.0 |

The result in Table 1 shows that the compound with Structural Formula (II) prepared in the first embodiment, and Compound 4 or Compound 5 synthetized in the fourth embodiment or the fifth embodiment can inhibit the activity of HMG-CoA reductase. Although the inhibitory effect of the compound on HMG-CoA reductase is worse than that of lovastatin, the inhibitory rate of the compound has reached 31.4%. Drug effect results show that in the same dosage, the activity of Compound 4 is higher than that of the compound with Structural Formula (II), and the inhibitory rate of Compound 4 is 37.8%. The result shows that the compound with Structural Formula (II) and Compound 4 have higher HMG-CoA reductase inhibitory activity, and the compound can be absolutely applied in preparing a drug with inhibitory effect on HMG-CoA reductase activity.

Although the present application only provides the preparation methods and HMG-CoA reductase inhibitory effect of the compounds in the first embodiment to the fifth embodiment, and has no description on preparation methods and HMG-CoA reductase inhibitory effect of each compound with Structural Formula (I), those skilled in the art are absolutely able to understand the preparation methods and HMG-CoA reductase inhibitory effect of other compounds based on the principle that compounds with similar structures have similar performance.

Thus it can be seen that the present application successfully extracts a compound with Structural Formula (I) from a Monascus-fermented rice preparation. There is no related report about the structural formula of the compound, and the compound is new. It is found through related experiments and studies that the compound has HMG-CoA reductase inhibitory effect to provide a brand new compound for preparing a drug which is capable of inhibiting HMG-CoA reductase and has a potential to be used as a drug for reducing or regulating blood lipid, or preventing and/or treating dyslipidemia, hyperlipidemia, hypercholesterolemia, or atherosclerosis, or improving vascular endothelial functions, or inhibiting platelet aggregation. Undoubtedly, this is good news for patients suffering from dyslipidemia, hyperlipidemia, hypercholesterolemia, atherosclerosis, endothelial dysfunction and platelet aggregation.

IV Anti-Cancer Effect Data of the Compounds Prepared by the First Embodiment, the Fourth Embodiment and the Fifth Embodiment 1. Experiment Materials 1.1 Cell Lines H22 purchased from Korean Cell Line Bank, Seoul, Korea;

S180, HepG-2, YAC-1, Thp1, U937 and B16-F10 purchased from Committee on Type Culture Collection of Chinese Academy of Sciences.

1.2 Drugs

The compounds with Structural Formula (II) prepared from the first embodiment to the third embodiment; Compound 4 prepared by the fourth embodiment and Compound 5 prepared by the fifth embodiment.

1.3 Reagents 3-(4,5-dimethylthiazol-2-yl)-2,5-diphenyltetrazolium bromide (MTT) purchased from Amresco; Roswell Park Memorial Institute (RPMI) 1640 and double-antibody purchased from Sigma; Fetal Bovine Serum (FBS) purchased from American Gibco; other reagents are domestic analytically pure reagents.

2. Experiment Method

Inoculatecancer cells in the logarithmic phase in each well of a 96-well culture plate ($2\times10^4$ cells/well); add the drugs until the final concentrations of the drugs are 500, 250, 125, 62.5, 31.25, 15.625 and 7.8125 μg/mL, after culturing the cancer cells for 72 hours in a cell incubator with a $CO_2$ concentration of 5%, add 10 μL of MTT to each well, incubate the cancer cells at 37° C. in darkness for 4 hours, remove the culture solution, add 150 μL of Dimethyl Sulfoxide (DMSO) or acidified isopropyl alcohol, after oscillating for 5 minutes, measure the Optical Density (OD) value at a wavelength of 570 nm; repeat the steps above for three times; set a blank control group; the cell lines use the same culture medium, which is a RPMI1640 culture medium containing 10% of FBS and 1% of double-antibody (penicillin and streptomycin).

3. Calculation Formula of Cell Viability

Cell viability=(experimental group OD value/control group OD value)×100%.

4. In-Vitro Anti-Cancer (Hepatoma and Lymphoma Drug) Activity of the Compound Prepared by the First Embodiment 4.1 In-Vitro Anti-Hepatoma Activity 4.1.1 Mouse Hepatoma Cell Line H22

Figure 9:
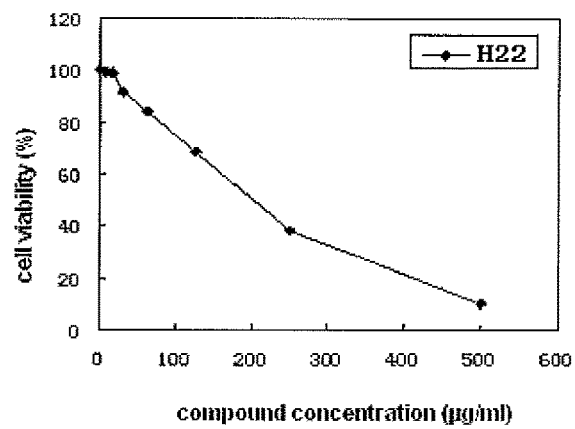
FIG. 9 shows a curve of inhibitory effect of a compound having Structural Formula (II) and prepared in the first embodiment on cell growth of mouse hepatoma cell line H22.

FIG. 9 is a curve of inhibitory effect of a compound with Structural Formula (II) prepared in the first embodiment on cell growth of mouse hepatoma cell line H22. It can be seen from FIG. 9 that, in an in-vitro anti-cancer (hepatoma) activity test performed for mouse hepatoma cell line H22 by using the compound with Structural Formula (II) prepared in the first embodiment, the compound with Structural Formula (II) has inhibitory effect on growth of mouse hepatoma cell line H22 in a concentration-effect relationship; the half maximal inhibitory concentration ($IC_{50}$) value is about 200 μg/mL, which indicates good inhibitory effect on mouse hepatoma cell proliferation.

Table 2 shows data indicating inhibition of Compound 4 and Compound 5 prepared by the fourth embodiment and the fifth embodiment on growth of mouse hepatoma cell line H22, and the result is as shown in Table 2:

TABLE 2

| Sample name | Cancer or tumour cell line | Sample concentration | Inhibitory rate |
|---|---|---|---|
| Compound 4 | Mouse hepatoma cell line H22 | 375 μg/mL | 45% |
| Compound 5 | Mouse hepatoma cell line H22 | 375 μg/mL | 42% |

It can be learned from the data in Table 2 that Compound 4 and Compound 5 prepared by the fourth embodiment and the fifth embodiment have obvious inhibitory effect on growth of mouse hepatoma cell line H22.

4.1.2 Mouse Hepatoma Cell Line HepG2

Figure 10:
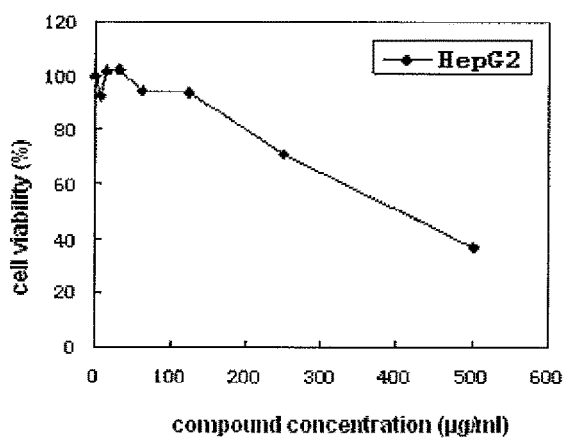
FIG. 10 shows a curve of inhibitory effect of a compound having Structural Formula (II) and prepared in the first embodiment on cell growth of mouse hepatoma cell line HepG2.

FIG. 10 is curve of inhibitory effect of a compound with Structural Formula (II) prepared in the first embodiment on cell growth of mouse hepatoma cell line HepG2. It can be seen from FIG. 10 that, in an in-vitro anti-cancer (hepatoma) activity test performed for mouse hepatoma cell line HepG2 by using the compound with Structural Formula (II) prepared in the first embodiment, the compound with Structural Formula (II) has inhibitory effect on growth of mouse hepatoma cell line HepG2 in a concentration-effect relationship; the $IC_{50}$ value is about 400 μg/mL, which indicates good inhibitory effect on mouse hepatoma cell proliferation.

4.1.3 Mouse Sarcoma Cell Line S180 (Sarcoma Grown in Liver Tissue)

Figure 11:
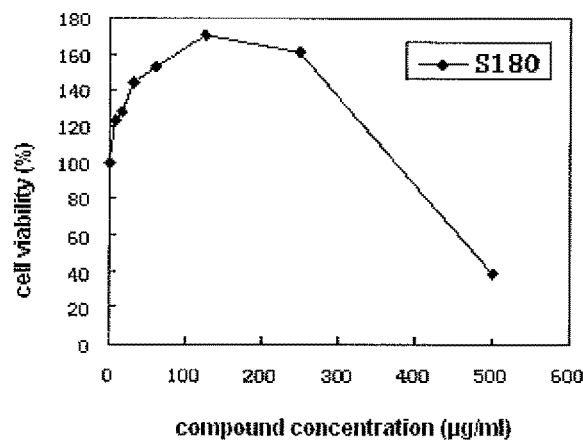
FIG. 11 shows a curve of inhibitory effect of a compound having Structural Formula (II) and prepared in the first embodiment on cell growth of mouse sarcoma cell line S180.

FIG. 11 is a curve of inhibitory effect of a compound with Structural Formula (II) prepared in the first embodiment on cell growth of mouse sarcoma cell line S180. It can be seen from FIG. 11 that, in an in-vitro anti-cancer (mouse sarcoma) activity test performed for mouse sarcoma cell line S180 by using the compound with Structural Formula (II) prepared in the first embodiment, the compound with Structural Formula (II) has inhibitory effect on growth of mouse sarcoma cell line S180 in a concentration-effect relationship; the $IC_{50}$ value is about 460 μg/mL, which indicates good inhibitory effect on mouse sarcoma cell proliferation.

4.2 In-Vitro Anti-Lymphoma Activity 4.2.1 Mouse Lymphoma Cells YAC-1

Figure 12:
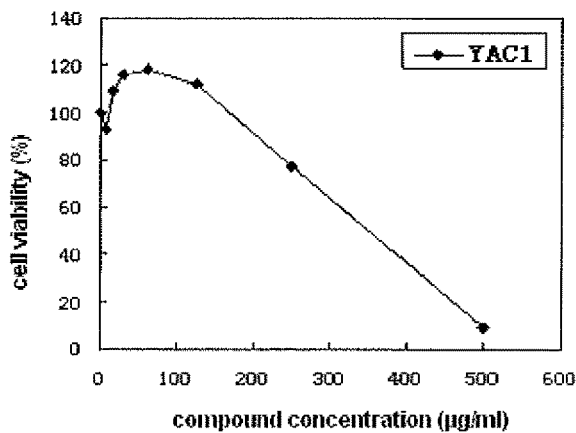
FIG. 12 shows a curve of inhibitory effect of a compound having Structural Formula (II) and prepared in the first embodiment on cell growth of mouse lymphoma cells YAC-1.

FIG. 12 is a curve of inhibitory effect of a compound with Structural Formula (II) prepared in the first embodiment on cell growth of mouse lymphoma cells YAC-1. It can be seen from FIG. 12 that, in an in-vitro anti-cancer (lymphoma) activity test performed for mouse lymphoma cells YAC-1 by using the compound with Structural Formula (II) prepared in the first embodiment, the compound with Structural Formula (II) has inhibitory effect on growth of mouse lymphoma cells YAC-1 in a concentration-effect relationship; the $IC_{50}$ value is about 350 μg/mL, which indicates good inhibitory effect on mouse lymphoma cell proliferation.

4.2.2 Human Mononuclear Lymphoma Cells THP1

Figure 13:
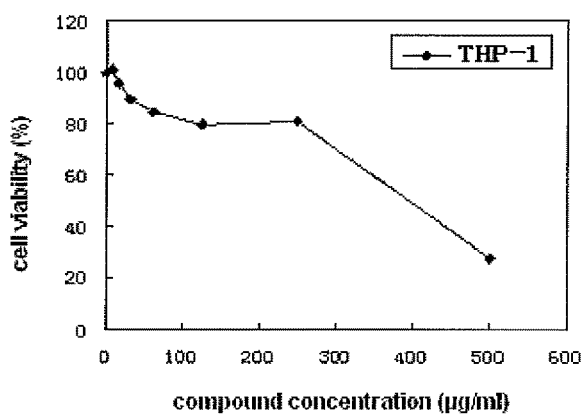
FIG. 13 shows a curve of inhibitory effect of a compound having Structural Formula (II) and prepared in the first embodiment on cell growth of human mononuclear lymphoma cells THP1.

FIG. 13 is a curve of inhibitory effect of a compound with Structural Formula (II) prepared in the first embodiment on cell growth of human mononuclear lymphoma cells THP1. It can be seen from FIG. 13 that, in an in-vitro anti-cancer (lymphoma) activity test performed for human mononuclear lymphoma cells THP1 by using the compound with Structural Formula (II) prepared in the first embodiment, the compound with Structural Formula (II) has inhibitory effect on growth of human mononuclear lymphoma cells THP1 in a concentration-effect relationship; the $IC_{50}$ value is about 400 μg/mL, which indicates good inhibitory effect on human mononuclear lymphoma cell proliferation.

4.2.3 Human Tissue Lymphoma Cells U937

Figure 14:
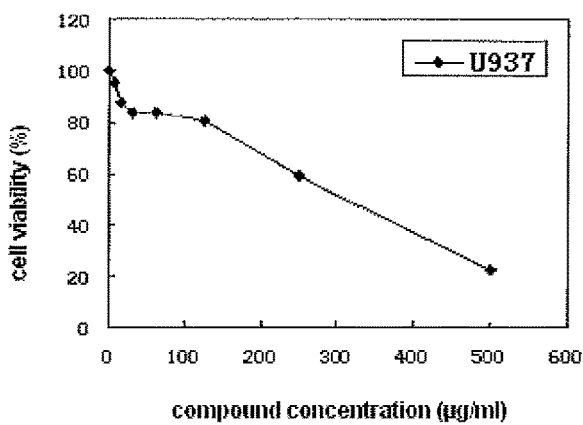
FIG. 14 shows a curve of inhibitory effect of a compound having Structural Formula (II) and prepared in the first embodiment on cell growth of human tissue lymphoma cells U937.

FIG. 14 is a curve of inhibitory effect of a compound with Structural Formula (II) prepared in the first embodiment on cell growth of human tissue lymphoma cells U937.

It can be seen from FIG. 14 that, in an in-vitro anti-cancer (lymphoma) activity test performed for human tissue lymphoma cells U937 by using the compound with Structural Formula (II) prepared in the first embodiment, the compound with Structural Formula (II) has inhibitory effect on growth of human tissue lymphoma cells U937 in a concentration-effect relationship; the $IC_{50}$ value is about 320 μg/mL, which indicates good inhibitory effect on human tissue lymphoma cell proliferation.

Table 3 shows data indicating the inhibition effect of Compound 4 and Compound 5 prepared by the fourth embodiment and the fifth embodiment on cell growth of human tissue lymphoma cells U937, and the result is as shown in Table 3:

TABLE 3

| Sample name | Cancer or tumour cell line | Sample concentration | Inhibitory rate |
|---|---|---|---|
| Compound 4 | Human tissue lymphoma cells U937 | 375 μg/mL | 39% |
| Compound 5 | Human tissue lymphoma cells U937 | 375 μg/mL | 47% |

It can be learned from the data in Table 3 that Compound 4 and Compound 5 prepared by the fourth embodiment and the fifth embodiment have obvious inhibitory effect on growth of human tissue lymphoma cells U937.

It can be seen from the test results that the present application extracts a compound with Structural Formula (I) from a *Monascus*-fermented rice preparation. There is no related report about the structural formula of the compound, and the compound is new. It is found through related experiments and studies that the compound has anti-cancer effect to provide a brand new compound for preparing a drug for preparing an anti-cancer drug, especially an anti-hepatoma drug and an anti-lymphoma drug. Undoubtedly, this is good news for cancer patients.

Although the present application only describes the preparation method and anti-cancer effect of the compound provided in the first embodiment in details, and has no description on preparation methods and effect of each compound with Structural Formula (I), those skilled in the art are absolutely able to understand the preparation methods and anti-cancer effect of other compounds based on the principle that compounds with similar structures have similar performance.

The above are only preferred embodiments of the present disclosure and should not be used for limiting the present disclosure. For those skilled in the art, the present disclosure may have various modifications and changes. Any modifications, equivalent replacements, improvements and the like within the spirit and principle of the present disclosure shall fall within the scope of protection of the present disclosure.

What is claimed is:

1. An isolated or modified sterol compound with Structural Formula (I) or a pharmaceutically acceptable salt thereof, wherein the Structural Formula (I) is as follows:

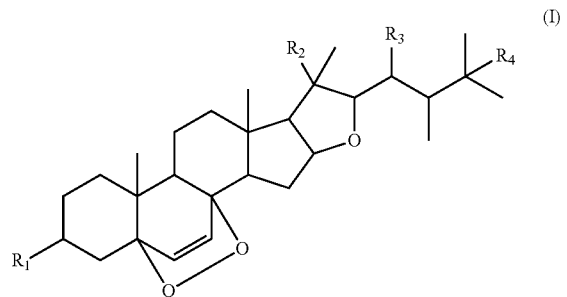

where $R_1$ is —OH, =O, H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH.

2. The isolated or modified sterol compound or the pharmaceutically acceptable salt thereof according to claim 1, wherein the sterol compound has Structural Formula (II) which is as follows:

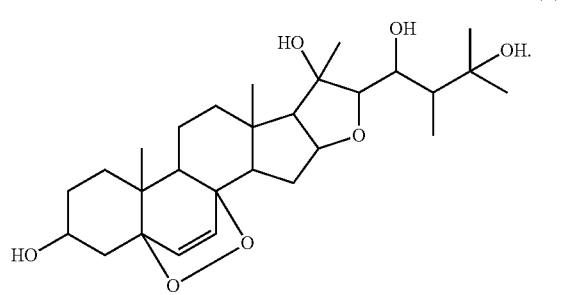

3. A modified sterol compound with structural formula (I) or the pharmaceutically acceptable salt thereof, wherein in the sterol compound with Structural Formula (I) is as follows:

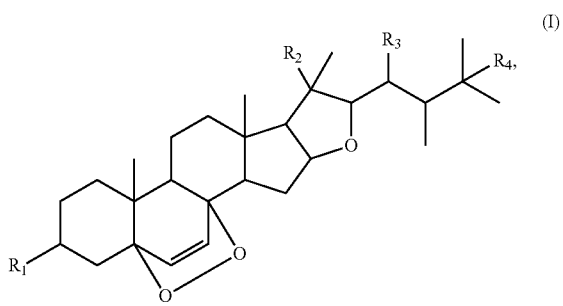

where, $R_1=R_2=R_3=R_4=$—OC(=O)—CH$_3$, or $R_1=R_2=R_3=R_4=$—OTs.

4. A preparation method for the sterol compound according to claim 1, wherein the preparation method comprises the following steps:
taking a *Monascus*-fermented rice preparation, performing ultrasonic extraction after adding a solvent, and concentrating an extract liquid under reduced pressure to obtain a refined extract;
performing column chromatography separation for the refined extract on silica gel, performing gradient elution for the refined extract by using petroleum ether and ethyl acetate during the separation process; volume ratios of petroleum ether to ethyl acetate during the gradient elution process are 75:25, 50:50 to 25:75 and 0:100 in turn;
using a mixed solution of dichloromethane and methanol with a volume ratio of 1:1 as the mobile phase, performing sephadex LH-20 gel column chromatography for an eluent obtained when the volume ratio of petroleum ether to ethyl acetate is 50:50 to 25:75, combining identical parts through Thin Layer Chromatography (TLC) tracking and detection to obtain 6 parts of fractions;
performing column chromatography separation for the fourth part of fractions, wherein the chromatographic column is a C18 reversed-phase silica gel column and the mobile phase is a mixed solution of methanol and water with a volume ratio of 75:25; through TLC detection, removing an impurity band and then collecting the sterol compound.

5. The preparation method according to claim 4, wherein the preparation method further comprises: performing silica gel column purification processing for the sterol compound, performing elution using a mixed solution of dichloromethane, ethyl acetate and methanol with a volume ratio of 20:20:1, and collecting the purified sterol compound after removing the impurity band.

6. The preparation method according to claim 4, wherein the solvent in the ultrasonic extraction process is one or more of petroleum ether, dichloromethane, ethyl acetate, ethanol, methanol or n-hexane with a volume which is 2 to 6 times as large as that of the *Monascus*-fermented rice preparation; and/or the number of extraction times during the ultrasonic extraction process is 2 to 6 times, each extraction lasts for 20 to 40 min; and/or the volume ratios of petroleum ether to ethyl acetate during the gradient elution are 75:25, 50:50, 25:75 and 0:100 in turn; sephadex LH-20 gel column chromatography is performed for an eluent obtained when the volume ratio of petroleum ether to ethyl acetate is 25:75.

7. A synthesis method for a sterol compound according to claim 2, wherein it comprises: mixing and dissolving a sterol compound with Structural Formula (III) and 5,10,15,20-tetraphenylporphyrin in a solvent, introducing oxygen at −5° C. to 5° C., performing column chromatography separation after a reaction to obtain a sterol compound with Structural Formula (II),

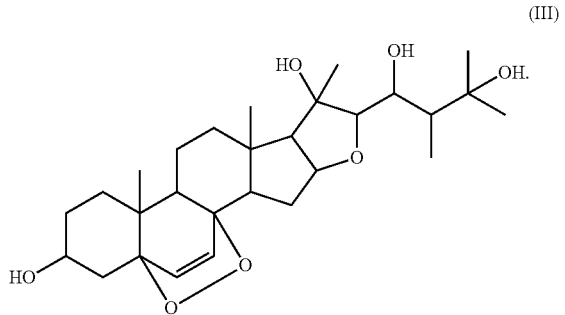 [SMILES: CC(C(O)C1OC2CC3C(C)(CCC4C35C=CC3(CC(O)CCC43C)OO5)C2C1(C)O)C(C)(C)O]

(III)

8. A synthesis method for the sterol compound according to claim 3, wherein the synthesis method comprises:
using a sterol compound with Structural Formula (III) as a raw material, generating ester/benzenesulfonate through derivatization, and then generating the sterol compound with Structural Formula (I) through oxidation, wherein $R_1=R_2=R_3=R_4=$—OC(=O)—CH$_3$, or $R_1=R_2=R_3=R_4=$—OTs;
or using the sterol compound with Structural Formula (III) as the raw material, generating a sterol compound with Structural Formula (II) through oxidation, and then generating the sterol compound with Structural Formula (I) through derivatization, wherein $R_1=R_2=R_3=R_4=$—OC(=O)—CH$_3$; or $R_1=R_2=R_3=R_4=$—OTs;
the Structural Formula (II) and the Structural Formula (III) are as follows:

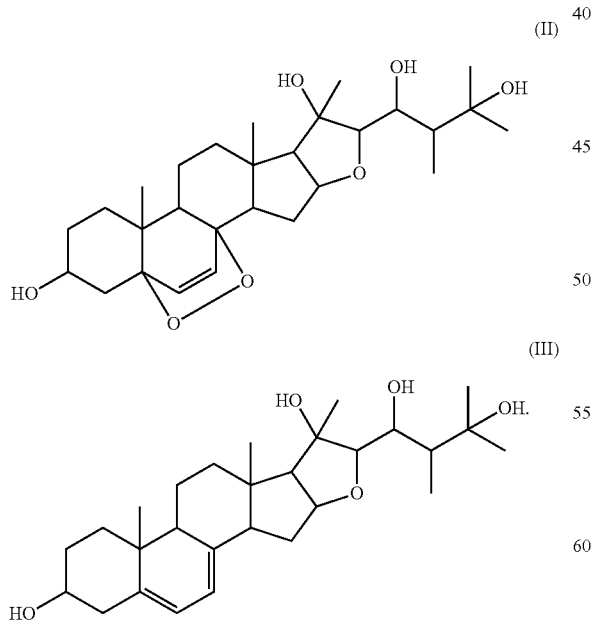

9. The synthesis method according to claim 8, wherein: when $R_1=R_2=R_3=R_4=$—OC(=O)—CH$_3$, the synthesis method comprises: performing catalytic reaction for a sterol compound with Structural Formula (II) and acetic anhydride to obtain the $R_1=R_2=R_3=R_4=$—OC(=O)—CH$_3$ sterol compound;
when $R_1=R_2=R_3=R_4=$—OTs, the synthesis method comprises: using triethylamine as an acid removal agent, performing a reaction for the sterol compound with Structural Formula (II) and p-toluenesulfonyl chloride with a molar ratio of 1:4 to 1:8 in dichloromethane to synthesize the $R_1=R_2=R_3=R_4=$—OTs sterol compound.

10. An extract, wherein the extract is:
(1) an eluent obtained by:
taking a *Monascus*-fermented rice preparation, performing ultrasonic extraction after adding a solvent, and concentrating an extract liquid under reduced pressure to obtain a refined extract;
performing column chromatography separation for the refined extract on silica gel, performing gradient elution for the refined extract by using petroleum ether and ethyl acetate during the separation process; volume ratios of petroleum ether to ethyl acetate during the gradient elution process are 75:25, 50:50 to 25:75 and 0:100 in turn, and obtaining an eluent when the volume ratio of petroleum ether to ethyl acetate is 50:50 to 25:75;
or
(2) the fourth part of fractions obtained by:
taking a *Monascus*-fermented rice preparation, performing ultrasonic extraction after adding a solvent, and concentrating an extract liquid under reduced pressure to obtain a refined extract;
performing column chromatography separation for the refined extract on silica gel, performing gradient elution for the refined extract by using petroleum ether and ethyl acetate during the separation process; volume ratios of petroleum ether to ethyl acetate during the gradient elution process are 75:25, 50:50 to 25:75 and 0:100 in turn; an eluent obtained when the volume ratio of petroleum ether to ethyl acetate is 50:50 to 25:75;
using a mixed solution of dichloromethane and methanol with a volume ratio of 1:1 as the mobile phase, performing sephadex LH-20 gel column chromatography for, combining identical parts through Thin Layer Chromatography (TLC) tracking and detection to obtain 6 parts of fractions, and the fourth part of fractions is obtained.

11. A composition, wherein the composition consists essentially of the sterol compound according to claim 1, and/or an extract containing the sterol compound, and a pharmaceutically acceptable carrier or an auxiliary material.

12. A method for preparing a drug for treatment or auxiliary treatment of hepatoma or lymphoma, comprising a step of mixing the sterol compound according to claim 1, or an extract containing the sterol compound, or a composition, the composition comprising the sterol compound, and/or the extract containing the sterol compound, and a pharmaceutically acceptable carrier or an auxiliary material.

13. A method for preparing a drug for reducing or regulating blood lipid, or treating dyslipidemia, hyperlipidemia, hypercholesterolemia, or atherosclerosis, or improving vascular endothelial functions, or inhibiting platelet aggregation, comprising a step of mixing the sterol compound according to claim 1, or an extract containing the sterol compound, or a composition, the composition comprising the sterol compound, and/or the extract containing the sterol compound with a pharmaceutically acceptable carrier or an auxiliary material.

14. A method for inhibiting 3-hydroxy-3-methylglutaryl-coenzyme A (HMG-CoA) in vivo or in vitro, comprising: using an effective amount of an HMG-CoA reductase inhibitor to inhibit the HMG-CoA reductase, wherein the HMG-CoA reductase inhibitor is the sterol compound according to claim 1, or an extract containing the sterol compound, or a composition, the composition comprising the sterol compound, and/or the extract containing the sterol compound, and optionally the composition further comprises a pharmaceutically acceptable carrier or an auxiliary material.

15. A method for inhibiting hepatoma or lymphoma cells in vivo or in vitro, comprising using an inhibitor to inhibit hepatoma or lymphoma cells, wherein the inhibitor comprises the sterol compound according to claim 1, or an extract containing the sterol compound, or a composition, the composition comprising the sterol compound, and/or the extract containing the sterol compound, and optionally the composition further comprises a pharmaceutically acceptable carrier or an auxiliary material.

16. A method for anti hepatoma or lymphoma, comprising a step of administering a dosage of the sterol compound with Structural Formula (I) at 0.001 to 1000 mg/kg bodyweight/day, wherein the Structural Formula (I) is as follows:

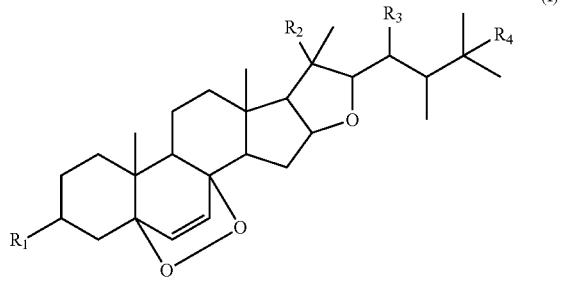

(I)

where $R_1$ is —OH, =O, H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH.

17. A method for treatment/or auxiliary treatment of reducing or regulating blood lipid, or treating dyslipidemia, hyperlipidemia, hypercholesterolemia, or atherosclerosis, or improving vascular endothelial function in the treatment of hepatoma or lymphoma, or inhibiting platelet aggregation, comprising a step of administering a dosage of the sterol compound with Structural Formula (I) at 0.001 to 1000 mg/kg bodyweight/day, wherein the Structural Formula (I) is as follows:

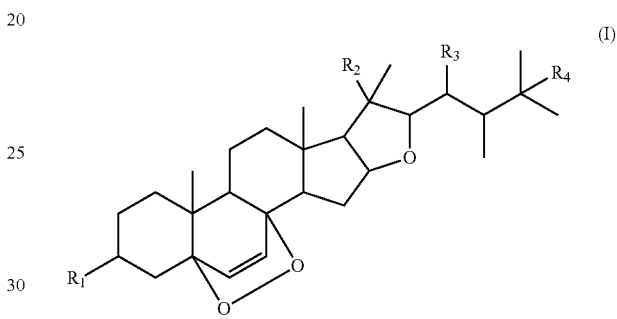

(I)

where $R_1$ is —OH, =O, H or C1-C3 alkyl; $R_2$ is —OH, H or C1-C3 alkyl; $R_3$ is —OH, =O, H or C1-C3 alkyl; $R_4$ is —OH, H or C1-C3 alkyl, and at least one of $R_1$, $R_2$, $R_3$ and $R_4$ is —OH.

* * * * *